US006696292B1

(12) United States Patent
Allen et al.

(10) Patent No.: US 6,696,292 B1
(45) Date of Patent: Feb. 24, 2004

(54) GENES ENCODING SULFATE ASSIMILATION PROTEINS

(75) Inventors: Stephen M. Allen, Wilmington (DE); Saverio Carl Falco, Arden (DE); Catherine J. Thorpe, Cambridge (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/720,317

(22) PCT Filed: Jul. 13, 1999

(86) PCT No.: PCT/US99/15810

§ 371 (c)(1),
(2), (4) Date: Dec. 21, 2000

(87) PCT Pub. No.: WO00/04154

PCT Pub. Date: Jan. 27, 2000

Related U.S. Application Data

(60) Provisional application No. 60/092,833, filed on Jul. 14, 1998.

(51) Int. Cl.[7] .......................... A01H 1/00; C07H 21/04; C07K 14/415; C12N 5/14; C12N 9/00

(52) U.S. Cl. .......................... 435/419; 435/6; 435/69.1; 435/183; 435/410; 435/252.3; 435/320.1; 530/370; 536/23.1; 536/23.2; 536/23.6; 536/24.1; 536/24.3; 536/24.33; 536/24.5; 800/278; 800/295

(58) Field of Search .......................... 435/6, 69.1, 183, 435/410, 419, 252.3, 320.1; 530/370; 536/23.1, 23.2, 23.6, 24.1, 24.3, 24.33, 24.5; 800/278, 295

(56) References Cited

PUBLICATIONS

Bork, P. Genome Research, vol. 10, 2000, p. 398–400.*

Lazar et al. Molecular and Cellular Biology, Mar. 1998 vol. 8, No. 3, p. 1247–1252.*

Burgess et al. The Journal of Cell Biology, 1990, vol. 111, p. 2129–2138.*

Brown et al. Science, Nov. 13, 1998, vol. 282, pp. 131–133.*

Ng et al. Plant Physiology, vol. 111, 651–652, 1996.*

Keiko Yonekura–Sakakibara et al., J. Biochem., vol. 124:615–621, 1998, Molecular Characterization of Tobaco Sulfite Reductase: Enzyme Purification, Gene Cloning, and Gene Expression Analysis.

Angelo Bolchi et al., Plant Mol. Biology, vol. 39:527–537, 1999, Coordinate Modulatin of Maize Sulfate Permease and ATP Sulfurylase mRNAs in Response to Variations in Sulfur Nutritional Status: Stereospecific Down–Regulation by L–Cysteine.

National Center for Biotechnology Information General Identifer No. 2967456, Oct. 22, 1999, Takahashi, H. et al., Identification of two leaf–specific sulfate transporters in *Arabidopsis thaliana*.

Hideki Takahashi et al., Plant Phys., vol. 121, 685–686, 1999, PGR 99–154, Identification of two leaf–specific sulfate transporters in *Arabidopsis thaliana*.

National Center for Biotechnology Information General Identifier No. 2285885, Jul. 30, 1997, Yamaguchi, Y. et al., Isolation and characterization of a cDNA encoding sulfate transporter from *arabidopsis thaliana*.

Yube Yamaguchi et al., Plant Phys., vol. 113:1463, 1997, PGR 97–051, Isolation of characterization of a cDNA encoding sulfate transporter from *arabidopsis thaliana*.

National Center for Biotechnology Information General Identifier No. 1217967, May 25, 2001, Smith, F.W. et al., Regulation of expression of a cDNA from barley roots encoding a high affinity sulphate transporter.

National Center for Biotechnology Information General Identifier No. 2738752, Mar. 31, 1999, Bolchi, A. et al., Coordinate modulation of maize sulfate permease and ATP sulfurylase mRNAs in response to variations in sulfur nutritional status: stereospecific down–regulation by L–cystein.

National Center for Biotechnology Information General Identifier No. 1711618, Oct. 1, 1996, Smith, F.W. et al., Plant members of a family of sulfate transporters reveal functional subtypes.

National Center for Biotechnology Information General Identifier No. 2626753, Nov. 20, 1997, Takahashi, H. et al., mRNA for sulfate transporter of *Arabidopsis thaliana*.

National Center for Biotechnology Information General Identifier No. 4579913, Feb. 20, 1999, Takahashi, H. et al., Sulfate transporter AST91 from *Arabidopsis thaliana*.

National Center for Biotechnololgy Information General Identifier No. 2130944, Oct. 22, 1999, Takahashi, H. et al., Identification of two leaf–specific sulfate transporters in *Arabidopsis thalian*.

National Center for Biotechnology Information General Identifier No. 1907270,M Nov. 26, 1997, Ng, A. et al., Isolation and characterization of a lowly expressed cDNA from the resurrection grass *Sporobolus stapfianus* with homology to eukaryote sulfate transporter proteins.

Smith, F. et al., Plant J., vol. 12(4):875–884, Regulation of expression of a cDNA from barley roots encoding a high affinity sulphate transporter.

EMBL Database Library Sequence No. AC D89631, 1997, Sohlberg L. and Sussex, I., Nucleotide sequence of a cDNA encoding a Cys proteinase from germinating bean cotyledons.

EMBL Database Library Sequence No. O49307, Jun. 1, 1998, Federspiel, N.A. et al.

EMBL Database Library Sequence No. D25000, Nov. 30, 1993, Minobe, Y. et al., Rice cDNA from root.

(List continued on next page.)

*Primary Examiner*—Phuong T. Bui

(57) ABSTRACT

This invention relates to an isolated nucleic acid fragment encoding a sulfate assimilation protein. The invention also relates to the construction of a chimeric gene encoding all or a portion of the sulfate assimilation protein, in sense or antisense orientation, wherein expression of the chimeric gene results in production of altered levels of the sulfate assimilation protein in a transformed host cell.

12 Claims, 13 Drawing Sheets

OTHER PUBLICATIONS

EMBL Database Library Sequence No. AF016306, Jan. 8, 1998, Bolchi, A. et al., Coordinate modulation of maize sulfate permease and ATP sulfurylase mRNAs in response to variations in sulfur nutritional status: stereospecific down–regulation by L–cysteine.

EMBL Database Library Sequence No. O48889, Jun. 1, 1998, Bolchi, A. et al.

EMBL Database Library Sequence No. X96761, Mar. 25, 1997, Ng, A. et al., Isolation of characterization of a lowly expressed cDNA from the resurrection grass *Sporobolus stapfianus* with homolgy to eukaryote sulfate transporter proteins.

Hideki Takahashi et al., PNAS, vol. 94:11102–11107, 1997, Regulation of sulfur assimilation in higher plants: A sulfate transporter induced in sulfate–starved roots plays a central role in *Arabidopsis thaliana*.

Hideki Takahashi et al., Plant and Cell Phys., vol. 39 suppl. pp. S148, 1998 Ann. Mtg. of Jap. Soc. of Plant Path., Tokyo, Japan, 1998, Antisense repression of sulfate transporters in transgenic *Arabidopsis thaliana* plants.

Smith, F. et al., PNAS, vol. 92:9373–9377, 1995, Plant members of a family of sulfate transporters reveal functional subtypes.

Arz, H.E. et al., Biochimica et Biophysica Acta, vol. 1218(3):447–452, 1994, A cDNA for adenylyl sulphate (APS)–kinase from *Arabidopsis thaliana*.

Bick, J.A. et al., Curr. Opin. in Plant Biol., vol. 1(3):240–244, 1998, Plant sulfur metabolism—reduction of sulfate to sulfite.

Schiffmann, S. et al., vol. 355:229–232, 1994, APS–sulfotransferase activity in identical to APS–kinase.

Jain, A. et al., Plant Phys., vol. 105:771–772, 1994, A cDNA clone for 5'–adenylylphosphosulfate kinase from *Arabidopsis thaliana*.

Chen, Y et al., Plant Phys., vol. 108(2):72, 1995, Sulfate–regulated expression of ATP sulfurylase and Adenosine–5'–phosphosulfate kinase in *brassica juncea*.

Lee, S. et al., Biochem. & Biophys. Res. Comm., vol. 247:171–175, APS kinase from *Arabidopsis thaliana*; genomic organization, expression, and kinetic analysis of the recombinant protein.

EMBL Sequence Data Library Accession No. AI637166, Walbot, V., 1999, Maize ESTs from various cDNA libraries sequenced at Stanford University.

Seyta, A. et al., PNAS, vol. 93:13383–13388, 1996, Sulfate reduction I n higher plants:molecular evidence for a novel 5'–adenylsulfate reductase.

Gutierrez–Marcos, J. F. et al., PNAS, vol. 93:13377–13382, 1996, Three members of a novel small gene–family from *Arabidopsis thaliana* able to complement functionally an *Escherichia coli* mutant defective in PAPS reductase activity encode proteins with a thioredoxin–like domain and "APS Reductase" activity.

Bick, J. A. et al., PNAS, vol. 95:8404–8409, 1998, Glutaredoxin function for the carboxyl–terminal domain of the plant–type 5'–adenylsulfate reductase.

Bick, J. A. et al., Curr. Opin. in Plant Biol., vol. 1(3):240–244, 1998, Plant sulfur metabolism—reduction of sulfate to sulfite.

Wray, J. L. et al., Chem. Biol. Inter., vol. 109(1–3):153–167, 1998, Redefining reductive sulfate assimilation in higher plants: a role for APS reductase, a new member of the thioredoxin family.

Heiss, S. et al., Plant Mol. Biol., vol. 39:847–857, 1999, Cloning sulfur assimilation genes from *Brassica juncea* L.: cadmium differentially affects the expression of a putative low–affinity sulfate transporter and isoforms of ATP sulfurylase and APS reductase.

Prior, A. et al., Biochimica acta, vol. 1430(1):25–38, 1999, Structural and kinetic properties of adenylyl sulfate reductase from *Catharanthus roseus* cell cultures.

EMBL Sequence Data Library Accession No: C27405, Aug. 6, 1997, Sasaki, T. et al., Rice cDNA from callus.

EMBL Sequence Data Library Accession No. AF071890, Jun. 29, 1998, Mbeguie–Mbeguie, D. et al., Molecular cloning and partial nucleotide sequence of a sulfite reductase from apricot fruit.

EMBL Sequence Data Library Accession No. D50679, Dec. 1, 1997, Ideguchi, T. et al., cDNA cloning and functional expression of ferredoxin–dependent sulfite reductase from maize in *E. coli* cells.

EMBL Sequence Data Library Accession No. O233813, Jan. 1, 1998, Ideguchi, T. et al.

Christine Bork et al., Gene, vol. 212:147–153, 1998, Isolation and characterization of a gene for assimilatory sulfite reductase from *Arabidopsis thaliana*.

Andreas WPI, Section Ch, Week 199440, Derwent Publications, Ltd. AN1994–321282 & JP 62 455773 A, Mitsubishi Corp., Sep. 1994.

Kasuki Saito et al., Journ. of Biol. Chem., vol. 270(27):16321–16323, 1995, Molecular cloning and characterization of a plant serine acetyltransferase playing a regulatory role in cysteine biosynthesis from watermelon.

Michael A. Roberts et al., Plant Mol. Biol., vol. 30:1041–1049, 1996, Cloning and characterization of an *Arabidopsis thaliana* cDNA clone encoding an organellar isoform of serine acetyltransferase.

EMBL Database Sequence Library Accession No. C26373, Aug. 8, 1997, Sasaki, T. et al., Rice cDNA from callus.

EMBL Database Sequence Library Accession No. P93544, May 1, 1997, Saito, K. et al.

Yoo, B et al., Plant Phys. suppl., vol. 114:267, 1997, Regulation of recombinant soybean serine acetyltransferase by CDPK.

Kasuki Saito et al., Comptes rendus de 'academie des sciences, vol. 319:969–973, 1996, Molecular characterization of cysteine biosynthetic enzymes in plants.

Kasuki Saito et al., Plant Phys., vol. 106:887–895, 1994, Modulation of cysteine biosynthesis in chloroplasts of transgenic tobacco overexpressing cysteine synthase.

Kasuki Saito et al., Stress responses of Photosynthetic Organisms, pp. 215–226, 1998, Molecular aspects of sulfur assimilation and acclimation to sulfur supply in plants.

EMBL Database Sequence Library Accession No. AC AU068082, 1999, Yamamoto, K. et al., Rice cDNA from callus.

EMBL Database Sequence Library Accession No. AQ688702, Jul. 2, 1999, Yu, Y. et al., a BAC and sequencing framework to sequence the rice genome.

* cited by examiner

```
                1                                                          60
SEQ ID NO:2     TREEEGRAIFRPTCRRCKPVSSHLSATDMVGMRGAYGGACNDDSKSRLHGGKAAEPEIAS
SEQ ID NO:4     HE----------------------------------------------------------
SEQ ID NO:6     TS----------------------------------------------------------
SEQ ID NO:8     SARARA------------------------------------------------------
SEQ ID NO:10    ------------------------------------------------------------
SEQ ID NO:12    MGSGSA---------------ANGGGGGAGAARVP-------------------------
SEQ ID NO:14    ------------------------------------------------------------
SEQ ID NO:16    ------------------------------------------------------------
SEQ ID NO:18    HELARTLSYITHICLLRNTIIEDMGSVD-------YEYPLGMNNFERVH-----------
SEQ ID NO:20    ---------------MVHHISD--EAAD--------EPSITTQTPPN---DPSQAPL---
SEQ ID NO:22    --------------------------------------TRAAMERARAMGP---------
SEQ ID NO:23    ----------------------------MVGMRVPYGGSYTNNGSNESQPP-GAAPEVPA
SEQ ID NO:24    -----------------------MGTED-------YTFPQGAEELHRRH-----------
SEQ ID NO:25    MS--------------------SLGTEQF---------------SERSQ-----------
SEQ ID NO:26    -----------------------MGTED-------YTFPQGAEELHRRH-----------
SEQ ID NO:27    ------------------------------------------------------------
SEQ ID NO:28    MSSKRASQY---------------------------------------------------
SEQ ID NO:29    ------------------------------------------------------------
SEQ ID NO:30    ---------------MPRTVSD--GGED-------FDGDVCSQTASQRHTDSTHHHH---
SEQ ID NO:31    MS------------------YASLSVKDLTSL-----VSRSGTGSSSSLKPPGQTRPVKV
```

FIG. 1A

```
                61                                                        120
SEQ ID NO:2     MA-VHKVAPPPARSTASKMKVRVKET-FFPDDPFRAFKGQPP-GTQWLMAVRYLFPILDW
SEQ ID NO:4     ------------------------------------------------------------
SEQ ID NO:6     ------------------------------------------------------------
SEQ ID NO:8     ------------------------------------------------------------
SEQ ID NO:10    ------------------------------------------------------------
SEQ ID NO:12    --------MPAAKPFLETLGGNMKET-FLPDDPFRVVRRERGCGRRAAAALRYVFPFMEW
SEQ ID NO:14    ------------------------------------------------------------
SEQ ID NO:16    --------HEPHQTTLHKLRHRVSEI-FFPDDPLHRFKNQTR-FKKFLLALQYLFPIFDW
SEQ ID NO:18    ----Q-VEVPPPQPFFKSLKYSLKET-FFPDDPLRQFKNKP-ASKKFMLGLQFFFPIFEW
SEQ ID NO:20    ---VYKVGYPPPKNLATEFTETLRET-FFHDNPLRQYKGQSGP-RRFMMGLEFLFPIFGW
SEQ ID NO:22    ------------------------------------W-----------EWAEAALPCLAW
SEQ ID NO:23    MVEVHKVVPPPPQSTASKLKTRLKET-LFPDDPFRGFQGQPA-RVQWVLAVKYLFPILDW
SEQ ID NO:24    ----HTVEAPQPQPFLKSLQYSVKET-LFPDDPFRQFKNQN-ASRKFVLGLKYFLPIFEW
SEQ ID NO:25    ----WVLNSPNPPPLTKKFLGPLKDNKFFTSSS-------SKKETRAVSFLASLFPILSW
SEQ ID NO:26    ----HTVEAPQPQPFLKSLQYSVKET-LFPDDPFRQFKNQN-ASRKFVLGLKYFLPIFEW
SEQ ID NO:27    ------------------------------------------------------------
SEQ ID NO:28    ----HQVEIPPPQPFLKSLKNTLNEI-LFADDPFRRIRNESKTSKKIELGLRHVFPILEW
SEQ ID NO:29    -MEVHKVVAPPHKSTVAKLKTKLKET-FFPDDPLRQFRGQPN-RTKLIRAAQYIFPILQW
SEQ ID NO:30    ---GYKVGFPPAKGVFAEFAEGVKET-FFADDPLREYKDQPRS-KKLWLSLVHLFPVLDW
SEQ ID NO:31    IPLQHPDTSNEARPPSIPF-----------DDIFSGWTAKIK-RMRLVDWIDTLFPCFRW
```

FIG. 1B

```
               121                                                        180
SEQ ID NO:2    VPSYSLS-LFKSDLVAGLTIASLAIPQGISYAKLASLPPIIGLYSSFVPPMVYAVLGSSR
SEQ ID NO:4    ----------ESDLIAGITIASLAIPQGISYAKLANLPPVLGLYSSFVPPLVYALMGSSK
SEQ ID NO:6    ------------------------------------------------------------
SEQ ID NO:8    ------------------------------------------------------------
SEQ ID NO:10   ------------------------------------------------------------
SEQ ID NO:12   APSYTLGT-LKSDLIAGTPLPASASRKG--------------------------------
SEQ ID NO:14   ------------------------------------------------------------
SEQ ID NO:16   APNYNLT-LLRSDLISGLTIASLAIPQGISYAKLANLPPILGLYSSFVPPLIYSLLGSSR
SEQ ID NO:18   APKYTFQ-FLKADLIAGITIASLAIPQGISYAKLANLPPILGLYSSFIPPLIYAMMGSSR
SEQ ID NO:20   GRDYSLN-KFKGDLIAGLTIASLCIPQDIGYSKLANLDPQYGLYSSFIPPLIYAAMGSSR
SEQ ID NO:22   MRSYRWKEDFQADLAAGITVGVMLVPQAMSYAKLAGLHPIYGLYTGFVPLFVYAIFGSSR
SEQ ID NO:23   LPAYSLS-LFKSDLIAGLTIASLAIPQGISYAKLANLPPLIGLYSSFVPPLVYAVLGSSR
SEQ ID NO:24   APRYNLK-FFKSDLIAGITIASLAIPQGISYAKLANLPPILGLYSSFVPPLVYAVLGSSR
SEQ ID NO:25   IRTYSAT-KFKDDLLSGLTLASLSIPQSIGYANLAKLDPQYGLYTSVIPPVIYALMGSSR
SEQ ID NO:26   APRYNLK-FFKSDLIAGITIASLAIPQGISYAKLANLPPILGLYSSFVPPLVYAVLGSSR
SEQ ID NO:27   ------------------------------------------------------------
SEQ ID NO:28   ARGYSLE-YLKSDVISGITIASLAIPQGISYAQLANLPPILGLYSSLVPPLVYAIMGSSR
SEQ ID NO:29   CPEYSFS-LLKSDVVSGLTIASLAIPQGISYANVANLPPIVGLYSSFVPPLVYAVLGSSR
SEQ ID NO:30   SRSYTFG-KFKGDLVAGLTIASLCIPQDIGYAKLANLQPHVGLYSSFVPPLIYALMGSSR
SEQ ID NO:31   IRTYRWSEYFKLDLMAGITVGIMLVPQAMSYAKLAGLPPIYGLYSSFVPVFVYAIFGSSR
```

FIG. 1C

```
                 181                                                        240
SEQ ID NO:2      DLAVGPVSISSLIMGS--MLRQAV-SPTAEPTLFLQLAFTSTLFAGLVQASLGILRLGFV
SEQ ID NO:4      DLAVGTVAVASLLISS--MLGSEV-SPTENPVLYLHLAFTATFFAGVFQASLGLLRLGFI
SEQ ID NO:6      ------------------------------------------------------------
SEQ ID NO:8      ------------------------------------------------------------
SEQ ID NO:10     ------------------------------------------------------------
SEQ ID NO:12     ------------------------------------------------------------
SEQ ID NO:14     ------------------------------------------------------------
SEQ ID NO:16     HLGVGPVSIASLVMGS--MLSDKI-SYTQEPILYLGLAFTATFFAGVFQASLGILRLGFV
SEQ ID NO:18     DLAVGTVAVGSLLMGS--MLSNAV-DPNEDPKLYLHLAFTATLFAGVFQAALGLFRLGLI
SEQ ID NO:20     DIAIGPVAVVSLLIGS--LLQAEV-DHVKNKEEYMRLAFTATFFAGITQAALGFLRLGFL
SEQ ID NO:22     QLAVGPVALVSLLVSN--VLGGIV---NSSSELYTELAILLAFMVGILECLMALLRLGWL
SEQ ID NO:23     DLAVGPVSISSLIMGPCCASRQPHCGADAVPAARLH----ATLFAGIFQASLGILRLGFI
SEQ ID NO:24     DLAVGTVAVASLLTGA--MLSKEV-DAEKDPKLYLHLAFTATFFAGVLEASLGIFRLGFI
SEQ ID NO:25     EIAIGPVAVVSMLLSS---LVPKVIDPDAHPNDYRNLVFTVTLFAGIFQTAFGVLRLGFL
SEQ ID NO:26     DLAVGTVAVASLLTGA--MLSKEV-DAEKDPKLYLHLAFTATFFAGVLEASLGIFRLGFI
SEQ ID NO:27     --AIGPVAVVSLLLGT--LLQNEI-DPKTHPLEYRRLAFTATFFAGVTQAALGFFRLGFI
SEQ ID NO:28     DLAVGTVAVASLLTAA--MLGKEV-NAVVNPKLYLHLAFTATFFAGLMQTCLGLLRLGFV
SEQ ID NO:29     DLAVGPVSIASLILGS--MLRQQV-SPVDDPVLFLQLAFSSTFFAGLFQASLGILRLGFI
SEQ ID NO:30     DIAIGPVAVVSLLLGT--LLQEEI-DPVKNPLEYSRLAFTATFFAGITQAMLGFFRLGFI
SEQ ID NO:31     QLAIGPVALVSLLVSN--ALGGIA---DTNEELHIELAILLALLVGILECIMGLLRLGWL
```

FIG. 1D

```
                241                                                        300
SEQ ID NO:2     IDFLSKATLVGFMAGAAIIVALQQLKGLLGIVHFTTEMGIVPVMASVFHHTSE-------
SEQ ID NO:4     VDLLSHATIVGFMAGAATVVCLQQLKGMLGLVHFTTSTDVVSVMESVFSQTHQ-------
SEQ ID NO:6     ------------------------------------------------------------
SEQ ID NO:8     ------------------------------------------------------------
SEQ ID NO:10    -----------------------------GIKSFTKKTDIISVMSXSPNRAHNR------
SEQ ID NO:12    ------------------------------------------------------------
SEQ ID NO:14    ------------------------------------------------------------
SEQ ID NO:16    IDFLSKATLVGFTGGAAIIVSLQQLKGLLGIVHFTSKMQIIPVTISVFKQRHE-------
SEQ ID NO:18    VDFLSHATIIGFMGGAATVVCLQQLKSILGLEHFTHGADIISVMRSVFTQTHE-------
SEQ ID NO:20    IEFLSHAAIVGFMGGAAITIALQQLKYVLGIANFTRKTDIVSVMESVWRSVHHG------
SEQ ID NO:22    IRFISHSVISGFTTASAIVIGLSQIKYFLGYS-VTRSSKIIPLIESI-------IAGIDQ
SEQ ID NO:23    IDFLSKATLVGFMAGAAIIVSLQQLKALLGIVHFTTEMGIVPVMASVFHHTKE-------
SEQ ID NO:24    VDFLSHATIVGFMGGAATVVSLQQLKGIFGLKHFTDSTDVISVMRSVFSQTHE-------
SEQ ID NO:25    VDFLSHAALVGFMAGAAIVIGLQQLKGLLGLTHFTTKTDAVAVLKSVYTSLHQQITSSEN
SEQ ID NO:26    VDFLSHATIVGFMGGAATVVSLQQLKGIFGLKHFTDSTDVISVMRSVFSQTHE-------
SEQ ID NO:27    IEFLSHAAIVGFMAGAAITIALQQLKGFLGIANFTKKSDIVSVMKSVWGNVHHG------
SEQ ID NO:28    VEILSHAAIVGFMGGAATVVCLQQLKGLLGLHHFTHSTDIVTVLRSIFSQSHM-------
SEQ ID NO:29    IDFLSKATLIGFMGGAAIIVSLQQLKGLLGITHFTKHMSVVPVLSSVFQHTNE-------
SEQ ID NO:30    IEFLSHAAIVGFMAGAAITIALQQLKGLLGIAKFTKKSDIISVMESVWGNVQHG------
SEQ ID NO:31    IRFISHSVISGFTSASAIVIGLSQIKYFLGYS-IARSSKIVPIVESI-------IAGADK
```

FIG. 1E

```
                301                                                        360
SEQ ID NO:2     WSWQTILMGVCFLVFLLSARHVSIRWPKLFWVSACAPLASVTISTLLVFLFKAQNHGISI
SEQ ID NO:4     WRWESVLLGCGFLFFLLVTRFISKRRPKLFWISAAAPLTSVVLGSVLVYLTHAENHGIEV
SEQ ID NO:6     ------------------------------------------------------------
SEQ ID NO:8     ------------------------------------------------------------
SEQ ID NO:10    WNWQTIVIGITFLAFLLLAKYIGKKNRKFFWVPAIAPITSVILATLFVFITRADKQGVQI
SEQ ID NO:12    ------------------------------------------------------------
SEQ ID NO:14    WHPGNFLIGCSFLIFILTTRFIGRRYKKLFWLSAISPLLSVILSTAAVYATRADRHGVKI
SEQ ID NO:16    WSWQTILLGFGFLVFLLTTRHISLRKPKLFWVSAAAPLTSVILSTILVFLLRNKTHQISV
SEQ ID NO:18    WRWESAVLGCVFIFFLLSTRYFSKKRPRFFWVSAMAPLTSVILGSLLVYFTHAEKHGVEV
SEQ ID NO:20    WNWQTIVIGVSFLVFLLFAKYIGKKKRKLFWVPAIAPIISVILATFFVYITRADKQGVQI
SEQ ID NO:22    FSWPPFVMGSAFLVILLIMKKLGKTNKKLRFLRASGPLTAVVLGTLFVKIFRP--TAISV
SEQ ID NO:23    WSWQTILMGVCFLVFLLVARHVSIRWPRLFWVSACAPLVSVIISTLVVFLFKAQNHGISI
SEQ ID NO:24    WRWESGVLGCGFLFFLLSTRYFSIKKPKFFWVAAMAPLTSVILGSLLVYFTHAERHGVQV
SEQ ID NO:25    WSPLNFVIGCSFLIFLLAARFIGRRNKKFFWLPAIAPLLSVILSTLIVFLSKGDKHGVNI
SEQ ID NO:26    WRWESGVLGCGFLFFLLSTRYFSIKKPKFFWVAAMAPLTSVILGSLLVYFTHAERHGVQV
SEQ ID NO:27    WNWQTILIGATFLAFLLVAKYIGKRNKKLFWVSAIAPLTSVIISTFFVYITRADKHGVAI
SEQ ID NO:28    WRWESGVLGCCFLIFLLTTKYISKKRPKLFWISAMSPLVSVIFGTIFLYFLHDQFHGIQF
SEQ ID NO:29    WSWQTIVMGVCFLLFLLSTRHLSMKKPKLFWVSAGAPLLSVIVSTLLVFVFRAERHGISV
SEQ ID NO:30    WNWQTILIGSSFLAFLLTTKYIAKKNKKLFWVSAIAPLISVVISTFCVYITRADKQGVAI
SEQ ID NO:31    FQWPPFVMGSLILVILQVMKHVGKAKKELQFLRAAAPLTGIVLGTTIAKVFHP--PSISL
```

FIG. 1F

```
                361                                                        420
SEQ ID NO:2     IGQLKCGLNRPSWDKLLFDTAYLGLTMKTGLVTGIISLTEGIAVGRTFASLKDYQIDGNK
SEQ ID NO:4     IGYLKKGLNPPSVTSLQFSPPYMMLALKTGIITGVIALAEGIAVGRSFAMFKNYHMTDNK
SEQ ID NO:6     -------------------------------------LTEAIAVGRSFASVRGYRLDGNK
SEQ ID NO:8     ------------------------------------------------------------
SEQ ID NO:10    VNHIKKGINPSSVHKIYFTGPFVAKGFKIGVISAMIGLTEAVAIGXTFAALKDYQLD---
SEQ ID NO:12    ------------------------------------------------------------
SEQ ID NO:14    IQKVHAGLNPSSVXQIHLNGPHTTECAQDRRHLRIIALTEAIAVGRSFASVRGYRLDGNK
SEQ ID NO:16    IGHLPKGVNPPSANMLYFNGPYLGLAIKTGIITGILSLTEGIAVGRTFASLKNYQVDGNK
SEQ ID NO:18    IGELKKGLNPPSLTNLVFVSPYMTTAVKTGIVVGIISLAEGIAVGRSFAMYKNYNIDGNK
SEQ ID NO:20    VKHIEQGINPSSVHKIYFTGPFVAKGFKIGVVCGIVGLTEAVAIGRTFAAMKDYQLDGNK
SEQ ID NO:22    VGEIPQGLPSFSIPRGF--EHLMSLMPTAILITGVAIL-ESVGIAKALAAKNGYELDSNK
SEQ ID NO:23    IGQLKCGLNRPSWDKTNIDTTYLGLTMKTGLVTGIISLTEGIAVGRTFASLKEYQIDGNK
SEQ ID NO:24    IGDLKKGLNPLSGSDLIFTSPYMSTAVKTGLITGIIALAEGIAVGRSFAMFKNYNIDGNK
SEQ ID NO:25    IKHVQGGLNPSSVHKLQLNGPHVGQAAKIGLISAIIALTEAIAVGRSFANIKGYHLDGNK
SEQ ID NO:26    ------------GSDLIFTSPYMSTAVKTGLITGIIALAEGVAVGRSFAMFKNYNIDGNK
SEQ ID NO:27    VKNIRKGINPPSASLIYFTGPYLATGFKIGIVAGMIGLTEAIAIGRTFAALKDYRIDGNK
SEQ ID NO:28    IGELKKGINPPSITHLVFTPPYVMLALKVGIITGVIALAEGIAVGRSFAMYKNYNIDGNK
SEQ ID NO:29    IGKLPEGLNPPSWNMLQFHGSHLALVAKTGLVTGIVSLTEGIAVGRTFAALKNYHVDGNK
SEQ ID NO:30    VKNIKQGINPPSFDLIYWSGPYLAKGFRIGVVSGMVALTEAIAIGRTFAAMKDYQIDGNK
SEQ ID NO:31    VGEIPQGLPTFSFPRSF--DHAKTLLPTSALITGVPIL-ESVGIAKALAAKNRYELDSNS
```

FIG. 1G

| | 421 480 |
|---|---|
| SEQ ID NO:2 | EMMAIGLMNVVGSCTSCYVTTGAFSRSAVNHNAGCKTAMSNVIMALTVMVTLLFLMPLFV |
| SEQ ID NO:4 | EMIAIGTMNVLGSLTSCYLTTGPFSRSAVNYNAGCRTAMSNVVMSLAVMVTLLFLTPLFH |
| SEQ ID NO:6 | EMLAMGFSNVAGSLSSCYVATGSFSRTAVNFSAGARSTVSNIVMSITVFVTLELFMKLLY |
| SEQ ID NO:8 | ------------------------------------------------------------ |
| SEQ ID NO:10 | ------------------------------------------------------------ |
| SEQ ID NO:12 | ------------------------------------------------------------ |
| SEQ ID NO:14 | EMLAMGFSNVAGSLSSCYVATGSFSRTAVNFSGGGQSTV--------------------- |
| SEQ ID NO:16 | EMMAIGLMNIAGSCSSCYVTTGSFSRSAVNYNAGAQTTVSNIIMAAAVLVTLLFLMPLFY |
| SEQ ID NO:18 | EMIAIGTMNVVGSFTSCYLTTGPFSRSAVNYNAGCKTAASNIIMSLAVMLTLLFLTPLFH |
| SEQ ID NO:20 | EMVALGTMNIVGSMTSCYVTTGSFSRSAVNFMAGCKTPVSNVVMSVVVLLTLLVITPLFK |
| SEQ ID NO:22 | ELFGLGLSNICGSFFSAYPATGSFSRSAVNHESGAKTGLSGIIMGIIICSALLFMTPLFT |
| SEQ ID NO:23 | EMMAIGLMNVVGSCTSCYVTTGAFSRSPVNHNAGCKTAMSNVIMALTVMVTLLFLMPLFV |
| SEQ ID NO:24 | EMIAFGMMNIVGSFTSCYLTTGPFSRSAVNYNAGCKTAMSNIVMAIAVMFTLLFLTPLFH |
| SEQ ID NO:25 | EMLAMGCMNIAGSLTSCYVSTGSFSRTAVNFSAGCKTAVSNIVMAVTVLLCLELFTRLLY |
| SEQ ID NO:26 | EMIAFGMMNIVGSFTSCYLTTGPFSRSAVNYNAGCKTAMSNIVMAIAVMFTLLFLTPLFH |
| SEQ ID NO:27 | EMVA-------------------------------------------------------- |
| SEQ ID NO:28 | EMIAFGMMNILGSFSSCYLTTGPFSRSAVNYNAGCKTALSNVVMAVAVAVTLLFLTPLFF |
| SEQ ID NO:29 | EMIAIGLMNVVGSATSCYVTTGAFSRSAVNNNAGAKTAVSNIVMSVTVMVTLLFLMPLFE |
| SEQ ID NO:30 | EMVALGTMNIVGSMTSCYVATGSFSRSAVNYMAGCKTAVSNVVMAIVVMLTLLLITPLFK |
| SEQ ID NO:31 | DLFGLGVANILGSLFSAYPATGSFSRSAVNNESEAKTGLSGLITGIIIGCSLLFLTPMFK |

FIG. 1H

| | 481 540 |
|---|---|
| SEQ ID NO:2 | YTPNVVLGAIIIAAVIGLIDFPAVYHIWKMDKMDFLVCVCAFAGVIFISVQEGLAIAVGI |
| SEQ ID NO:4 | YTPLVVLSAIIVSAMLGLVDFGAALHLWRVDKVDFCVCAGAYLGVVFGSVEVGLVVAVAV |
| SEQ ID NO:6 | YTPMAVLASIILSALPGLIDIKEACSIWKIDKMDFLTCLGAFVGVLFGSVEIGLAVALGI |
| SEQ ID NO:8 | -----------------------AIHLWTLDKFDFVVCMSAYFGVVFGSVEIGLVIAVAL |
| SEQ ID NO:10 | ---------------------------WN------------------------------- |
| SEQ ID NO:12 | ------------------------------------------------------------ |
| SEQ ID NO:14 | ------------------------------------------------------------ |
| SEQ ID NO:16 | YTPNVVLAAIIITAVIGLIDYQSAYKLWKVDKLDFLACLCSFFGVLFISVPLGLGIAVII |
| SEQ ID NO:18 | YTPLVVLSAIIVSAMLGLIDYEAAIHLFKVDKFDFVVCMSAYIGVVFGSVEIGLVIAIVI |
| SEQ ID NO:20 | YTPNAILGSIIISAVIGLVDYEAAILIWKVDKLDFIACMGAFFGVVFVSVEIGLLIAVAI |
| SEQ ID NO:22 | DIPQCALAAIVISAVTGLVDYEEAIFLWGIDKKDFFLWAMTFTTTLTFGIEIGVLVGVGF |
| SEQ ID NO:23 | YTPNVVLGAIIIAAVIGLIDIPAVYHIWKMDKMDFLVCVCAFAGVLFISVQEGLAIAVGI |
| SEQ ID NO:24 | YTPLVVLSAIIISAMLGLIDYQAAIHLWKVDKFDFLVCMSAYVGVVFGSVEIGLVVAVAI |
| SEQ ID NO:25 | YTPMAILASIILSALPGLIDIGEAYHIWKVDKFDFLACLGAFFGVLFVSIEIGLLIALSI |
| SEQ ID NO:26 | YTPLVVLSAIIISAMLGLIDYQAAIHLWKVDKFDFLVCMSAYVGVVFGSVEIGLVVAVAI |
| SEQ ID NO:27 | ------------------------------------------------------------ |
| SEQ ID NO:28 | YTPLVVLSSIIIAAMLGLVDYEAAIHLWKLDKFDFFVCLSAYLGVVFGTIEIGLILSVGI |
| SEQ ID NO:29 | YTPNVVLGAIIVTAVIGLIDLPAACHIWKIDKFDFLVMLCAFFGVIFLSVQNGLAIAVGL |
| SEQ ID NO:30 | YTPNAILASIIINAVVNLVDYETAYLIWKVDKMDFVALLGAFFGVVFASVEYGLLIAVAI |
| SEQ ID NO:31 | YIPQCALAAIVISAVSGLVDYDEAIFLWRVDKRDFSLWTITSTITLFFGIEIGVLVGVGF |

FIG. 11I

| | |
|---|---|
| | 541 600 |
| SEQ ID NO:2 | SIFRVLMQITRPKMMVQGNIKGTDIYRDLHHYKEAQRVSGFLILAIEAP-INFANSNYLN |
| SEQ ID NO:4 | SLLRVLLFVARPRTTVLGNIPGTMVYRRMDQYAAAQTVPGVLVLRVDAP-VYFANASYLR |
| SEQ ID NO:6 | SFAKIIIQSLRPQVEILGRLQGTDIFCSVRQYPVACLTPTVLPIRVDTSFLCFINATSVK |
| SEQ ID NO:8 | SLLRVLLFVSRPRTSTLGLIPDSTIYRSMDQYQNAKSVPGILILQIEAP-IYFANSSYLR |
| SEQ ID NO:10 | ------------------------------------------------------------ |
| SEQ ID NO:12 | ------------------------------------------------------------ |
| SEQ ID NO:14 | ------------------------------------------------------------ |
| SEQ ID NO:16 | SVLKILLHVTRPNTLVLGNIPGTQIFHNINQYKKALRVPSFLILAVESP-IYFANSTYLQ |
| SEQ ID NO:18 | SVLRVLLFIARPRTFVLGNIPNSVIYRNVLn:QNAKHVPGMLILEIDAP-IYFANASYLR |
| SEQ ID NO:20 | SFAKILLQVTRPRTALLGNLPGTTIYRNISQYPEAKLTPGVVIVRVDSA-IYFSNSNYVR |
| SEQ ID NO:22 | SLAFVIHESANPHIAVLGRLPGTTVYRNTLQYPEAYTYNGIVVVRVDAP-IYFANISYIK |
| SEQ ID NO:23 | SVFRVLLQITRPKITVQGNIMGTDIYRNLHQYKDAQRIPGFLILATEAP-INFANSNYLN |
| SEQ ID NO:24 | SIARLLLFVSRPKTAVKGNIPNSMIYRNTEQYPSSRTVPGILILEIDAP-IYFANASYLR |
| SEQ ID NO:25 | SFAKILLQAIRPGVEVLGRIPTTEAYCDVAQYPMAVTTPGILVIRISSGSLCFANAGFVR |
| SEQ ID NO:26 | SIARLLLFVSRPKTAVKGNIPNSMIYRNTEQYPSSRTVPGILILEIDAP-IYFANASYLR |
| SEQ ID NO:27 | ------------------------------------------------------------ |
| SEQ ID NO:28 | SVMRLVLFVGRPKIYVMGNIQNSEIYRNIEHYPQAITRSSLLILHIDGP-IYFANSTYLR |
| SEQ ID NO:29 | SLFKILMQVTRPKMVIMGNIPGTDIYRDLHHYKEAQRIPGFLVLSIESP-VNFANSNYLT |
| SEQ ID NO:30 | SLGKILLQVTRPRTALLGNLPRTTIYRNVEQYPEATKVPGVMIVRVDSA-IYFTNSNYVK |
| SEQ_ID_NO:31 | SLAFVIHESANPHIAVLGRLPGTTVYRNIKQYPEAYTYNGIVIVRIDSP-IYFANISYIK |

FIG. 1J

```
                601                                                        660
SEQ ID NO:2     ERIKRWI-EE--ESFEQDKHTELHFIILDLSAVPAIDTSGIAFLIDIKKSIEKRGLELVL
SEQ ID NO:4     ERISRWI-DDEEERTKSQGEMGVRYVVLDMGAIGSIDTSGTSMLDELNKSLDRRGMQIVL
SEQ ID NO:6     ERITEWVWEGVETS-NGKARERIQAVVLDMSSVVNIDTSGLTALEEIHKELVSLGLQMAI
SEQ ID NO:8     ERIVRWV-DEEEDRLKSLKENDLQYVILALSAVGNIDTSGITMLGEVKKVMERRGLKLVL
SEQ ID NO:10    -----------------------------------------------------KEM----
SEQ ID NO:12    ------------------------------------------------------------
SEQ ID NO:14    ------------------------------------------------------------
SEQ ID NO:16    ERILRWV-REEEEHIKANNGAPLKCIILDMTAVTATDTSGLDTLCELRKMLEKRSLEFVL
SEQ ID NO:18    ERITRWI-DEEEERIKATGETSLQYVIIDMSAVGNIDTSGISMLEEVKKITERRELQLVL
SEQ ID NO:20    ERILRWL-TDEEDRAKAVGLPKISFLIVEMSPVIDIDTSGIHALEDLYKNLQKKDMQLIL
SEQ ID NO:22    DRLREYELKLPN-SNRGPDVGRVYFVILEMSPVTYIDSSAVQALKDLHQEYKARDIQIAI
SEQ ID NO:23    ERIKRWI-EE--ESSAQTKQTELRFVILDLSAVPAIDTSGVAFLIDIKKSIEKRGLELVL
SEQ ID NO:24    ERIIRWI-DEEEERVKQSGESSLQYIILDMSAVGNIDTSGISMMVEIKKVIDRRALKLVL
SEQ ID NO:25    ERILKWVEDEEQDNIEEAAKGRVQAIIIDMTDLTNVDTSGILALEELHKKLLSRGVELAM
SEQ ID NO:26    ERIIRWI-DEEEERVKQSGESSLQYIILDMSAVGNIDTSGISMMVEIKKVIDRRALKLVL
SEQ ID NO:27    ------------------------------------------------------------
SEQ ID NO:28    DRIGRWI-DEEEDKLRTSGDISLQYIVLDMSAVGNIDTSGISMLEELNKILGRRELKLVI
SEQ ID NO:29    ERTSRWI-EECEEEEAQEKHSSLQFLILEMSAVSGVDTNGVSFFKELKKTTAKKDIELVF
SEQ ID NO:30    ERILRWL-RDEEEQQQEQKLSKTEFLIVELSPVTDIDTSGIHALEELLKALEKRKIQLIL
SEQ ID NO:31    DRLREYEVAVDKYTNRGLEVDRINFVILEMSPVTHIDSSAVEALKELYQEYKTRDIQLAI
```

FIG. 1K

```
               661                                                        720
SEQ ID NO:2    VNPTGEVMEKIQRANEAENYFRPD--CLYLTTGEAIAS----------------------
SEQ ID NO:4    ANPGSEIMKKLDSSKVL-EQIGHEW--VFPTVGEAVASC--------------DYVLHSH
SEQ ID NO:6    ASPGWKAVQKMKVSQVV-DRVGQDW--IFMTVGEAVEAC-----------------LAAH
SEQ ID NO:8    ANPGGEVIKKMNKAKLIEV-IGQEW--IYLTVGEAVGAC--------------NFMLHTY
SEQ ID NO:10   ------------------------------------------------------------
SEQ ID NO:12   ------------------------------------------------------------
SEQ ID NO:14   ------------------------------------------------------------
SEQ ID NO:16   ANPVGNVMEKLHKSNILDSF---GLKGVYLTVGEAVTD----------------------
SEQ ID NO:18   VNPVSEVMKKLNKSKF-QNHLGKKW--IYLTVEEAVGAC--------------NFNLRAS
SEQ ID NO:20   SNPGSVVIEKLQASKL-TEHIGSSN--IFLAVSDAVRFC--------------T------
SEQ ID NO:22   ANPNRQVHLLLSRAGII-DMIGAGW--CFVRVHDAVQVCLQHVRSS--------------
SEQ ID NO:23   VNPTGEGHGKNTASERGTQAFQVGIACI-LTTGEAVAS----------------------
SEQ ID NO:24   SNPKGEVVKKLTRSKFIGDHLGKEW--MFLTVGEAVEAC--------------SYMLHTF
SEQ ID NO:25   VNPRWEVIHKLKVANFV-DKIGKER--VFLTVAEAVDAC-----------------LSSR
SEQ ID NO:26   SNPKGEVVKKLTRSKFIGDHLGKEW--MFLTVGEAVEAC--------------SYMLHTF
SEQ ID NO:27   ------------------------------------------------------------
SEQ ID NO:28   ANPGAEVMKKLSKSTFIES-IGKER--IYLTVAEAVAAC--------------DFMLHTA
SEQ ID NO:29   VNPLSEVVEKLQRADEQKEFMRPEF--LFLTVAEAVAS----------------------
SEQ ID NO:30   ANPGPAVIQKLRSAKF-TDLIGDDK--IFLSVGDAVKKF--------------A------
SEQ ID NO:31   SNPNKDVHLTIARSGMV-ELVGKEW--FFVRVHDAVQVCLQYVQSSNLEDKHLSFTRRYG
```

FIG. 1L

```
               721                  742
SEQ ID NO:2    -----------LSALA-KMTKP
SEQ ID NO:4    K------PGMAKDSAAAHESMV
SEQ ID NO:6    KGTA---------------LAC
SEQ ID NO:8    KNAEKPTSGSESGKESRNDNNV
SEQ ID NO:10   ----------------------
SEQ ID NO:12   ----------------------
SEQ ID NO:14   ----------------------
SEQ ID NO:16   -----------ISSI--WKAQP
SEQ ID NO:18   K------TNPKKDETEGWNN-V
SEQ ID NO:20   ---------------TKSMQEP
SEQ ID NO:22   ------------------SSNA
SEQ ID NO:23   -----------LSALA-KMASP
SEQ ID NO:24   K------TEPASKN-EPWNN-V
SEQ ID NO:25   --FA---------------NSA
SEQ ID NO:26   K------TEPASKN-EPWNN-V
SEQ ID NO:27   ----------------------
SEQ ID NO:28   K------PDSPVPEFNN----V
SEQ ID NO:29   -----------LSLKGPSLSNV
SEQ ID NO:30   ---------------PKSSLNV
SEQ ID NO:31   GSNNNSSSSNALLKEPLLSVEK
```

FIG. 1M

SEQUENCE LISTING

```
<160> NUMBER OF SEQ ID NOS: 31

<210> SEQ ID NO 1
<211> LENGTH: 2279
<212> TYPE: DNA
<213> ORGANISM: Zea mays

<400> SEQUENCE: 1

gcacgagaga agaagaagga agggccatct tccgacccac ttgtaggcgc tgtaagcctg     60

taagcagtca cctctcagcc acagacatgg tgggcatgag aggcgcctac ggtggtgctt    120

gcaatgacga cagcaagagc cggctgcacg gaggcaaggc ggcggagccg gagatcgcgt    180
```

-continued

```
cgatggcagt gcacaaggtg gcgccgccac cggcgcggag cacggcgagc aagatgaagg    240

tgagggtgaa ggagaccttc ttccccgacg acccgttccg ggcgttcaag gggcagccgc    300

cggggacgca gtggctcatg gcggtcaggt acctcttccc catcctggac tgggtgccga    360

gctactcctt gtcgctcttc aagtccgacc tcgtcgcggg cctcaccatt gccagcctcg    420

ccattcctca gggcattagc tacgcgaagc tggcaagctt gcctcccata atcgggctgt    480

attcgagctt cgtgccgccg atggtgtacg cggtgctggg gagctcccgt gacctggcgg    540

tgggcccggt gtcgatctcg tcgctgatca tggggtccat gctgcggcag gccgtgagcc    600

ccactgcgga gccgacgctg ttcctgcagc tggccttcac ctccaccctg ttcgcggggc    660

tggtgcaggc ctccctgggc atcctcaggc tcggcttcgt catcgacttc ctgtccaagg    720

cgacgctggt ggggttcatg gccggcgccg ccatcatcgt ggcgctgcag caactcaagg    780

ggctgctggg catcgtccac ttcaccaccg agatgggcat cgtcccagtc atggcctccg    840

tcttccacca caccagcgag tggtcgtggc agacgatcct catgggcgtc tgcttcctcg    900

tcttcctgct gtcggcgagg catgtgagca tcagatggcc aaagcttttc tgggtttcgg    960

cgtgcgcgcc cctggcatcg gtcaccatct cgacgctgct tgttttcctc ttcaaagctc   1020

agaaccatgg catcagcatc attgggcagc tcaagtgcgg cctgaatcgc ccctcgtggg   1080

acaagctcct gtttgacacg gcgtatttag gcctcaccat gaagactggc cttgtcaccg   1140

gaatcatctc actgacggaa ggaatagcgg ttggtagaac atttgcctca ctcaaggact   1200

accagataga tggaaacaag gagatgatgg ccatagggtt gatgaatgtt gttgggtcct   1260

gcacatcatg ctacgtaaca acaggtgcgt tctcccgctc tgctgtaaac cacaacgccg   1320

gctgcaagac tgccatgtcc aacgtgatca tggcgctgac tgtgatggtc acgctgctgt   1380

tcctcatgcc actgttcgtg tacacaccca acgttgtcct cggagcgatc atcatcgccg   1440

cggtgatcgg cctgatcgat ttccccgcgg tgtaccacat ctggaagatg gacaagatgg   1500

attttctggt gtgcgtttgc gcgtttgccg gcgtcatctt catctcagtc caagaaggcc   1560

ttgcgatagc ggttggtata tctatattta gggtgttgat gcagatcaca aggccgaaga   1620

tgatggttca agggaacatc aaggggactg atatttacag agacctgcat cactacaagg   1680

aggcccaaag agtttctggg ttcttgatct tggccattga agcaccgata aacttcgcca   1740

actccaacta cctgaatgaa aggattaaaa gatggataga ggaagaatct tttgaacagg   1800

ataaacatac tgaactccat ttcataatct tggatctgtc agctgttcct gcaattgaca   1860

caagtggcat agcgttcctc attgacataa agaaatcaat agagaaacgt ggtctggagc   1920

ttgtgcttgt caatccaact ggagaagtca tggagaaaat acaacgtgca aacgaggctg   1980

aaaactattt taggccagat tgcttgtatc tgaccactgg cgaagcaatc gcttcacttt   2040

ctgcacttgc caagatgaca aaaccctaaa tggattgctg aattgtcatt gtgttcatcc   2100

ctagcactgt taaaagtttt cggtgcagga ttttctgtaa tggggagtgc atccaatagg   2160

agtacatcac agctatgttt gtatctagta gaattcttca gatccatgtg atgcaaattc   2220

aatggaaaac aaatatgaca gtacaatagt agatcttaca gaaattttct gctgcaaaa    2279
```

<210> SEQ ID NO 2
<211> LENGTH: 688
<212> TYPE: PRT
<213> ORGANISM: Zea mays

<400> SEQUENCE: 2

Thr Arg Glu Glu Glu Gly Arg Ala Ile Phe Arg Pro Thr Cys Arg Arg

-continued

```
1               5                   10                  15

Cys Lys Pro Val Ser Ser His Leu Ser Ala Thr Asp Met Val Gly Met
            20                  25                  30

Arg Gly Ala Tyr Gly Gly Ala Cys Asn Asp Asp Ser Lys Ser Arg Leu
        35                  40                  45

His Gly Gly Lys Ala Ala Glu Pro Glu Ile Ala Ser Met Ala Val His
    50                  55                  60

Lys Val Ala Pro Pro Pro Ala Arg Ser Thr Ala Ser Lys Met Lys Val
65                  70                  75                  80

Arg Val Lys Glu Thr Phe Phe Pro Asp Asp Pro Phe Arg Ala Phe Lys
                85                  90                  95

Gly Gln Pro Pro Gly Thr Gln Trp Leu Met Ala Val Arg Tyr Leu Phe
            100                 105                 110

Pro Ile Leu Asp Trp Val Pro Ser Tyr Ser Leu Ser Leu Phe Lys Ser
        115                 120                 125

Asp Leu Val Ala Gly Leu Thr Ile Ala Ser Leu Ala Ile Pro Gln Gly
    130                 135                 140

Ile Ser Tyr Ala Lys Leu Ala Ser Leu Pro Pro Ile Ile Gly Leu Tyr
145                 150                 155                 160

Ser Ser Phe Val Pro Pro Met Val Tyr Ala Val Leu Gly Ser Ser Arg
                165                 170                 175

Asp Leu Ala Val Gly Pro Val Ser Ile Ser Ser Leu Ile Met Gly Ser
            180                 185                 190

Met Leu Arg Gln Ala Val Ser Pro Thr Ala Glu Pro Thr Leu Phe Leu
        195                 200                 205

Gln Leu Ala Phe Thr Ser Thr Leu Phe Ala Gly Leu Val Gln Ala Ser
    210                 215                 220

Leu Gly Ile Leu Arg Leu Gly Phe Val Ile Asp Phe Leu Ser Lys Ala
225                 230                 235                 240

Thr Leu Val Gly Phe Met Ala Gly Ala Ala Ile Ile Val Ala Leu Gln
                245                 250                 255

Gln Leu Lys Gly Leu Leu Gly Ile Val His Phe Thr Thr Glu Met Gly
            260                 265                 270

Ile Val Pro Val Met Ala Ser Val Phe His His Thr Ser Glu Trp Ser
        275                 280                 285

Trp Gln Thr Ile Leu Met Gly Val Cys Phe Leu Val Phe Leu Leu Ser
    290                 295                 300

Ala Arg His Val Ser Ile Arg Trp Pro Lys Leu Phe Trp Val Ser Ala
305                 310                 315                 320

Cys Ala Pro Leu Ala Ser Val Thr Ile Ser Thr Leu Leu Val Phe Leu
                325                 330                 335

Phe Lys Ala Gln Asn His Gly Ile Ser Ile Ile Gly Gln Leu Lys Cys
            340                 345                 350

Gly Leu Asn Arg Pro Ser Trp Asp Lys Leu Leu Phe Asp Thr Ala Tyr
        355                 360                 365

Leu Gly Leu Thr Met Lys Thr Gly Leu Val Thr Gly Ile Ile Ser Leu
    370                 375                 380

Thr Glu Gly Ile Ala Val Gly Arg Thr Phe Ala Ser Leu Lys Asp Tyr
385                 390                 395                 400

Gln Ile Asp Gly Asn Lys Glu Met Met Ala Ile Gly Leu Met Asn Val
                405                 410                 415

Val Gly Ser Cys Thr Ser Cys Tyr Val Thr Thr Gly Ala Phe Ser Arg
            420                 425                 430
```

-continued

```
Ser Ala Val Asn His Asn Ala Gly Cys Lys Thr Ala Met Ser Asn Val
        435                 440                 445

Ile Met Ala Leu Thr Val Met Val Thr Leu Leu Phe Leu Met Pro Leu
    450                 455                 460

Phe Val Tyr Thr Pro Asn Val Val Leu Gly Ala Ile Ile Ile Ala Ala
465                 470                 475                 480

Val Ile Gly Leu Ile Asp Phe Pro Ala Val Tyr His Ile Trp Lys Met
                485                 490                 495

Asp Lys Met Asp Phe Leu Val Cys Val Cys Ala Phe Ala Gly Val Ile
            500                 505                 510

Phe Ile Ser Val Gln Glu Gly Leu Ala Ile Ala Val Gly Ile Ser Ile
        515                 520                 525

Phe Arg Val Leu Met Gln Ile Thr Arg Pro Lys Met Met Val Gln Gly
    530                 535                 540

Asn Ile Lys Gly Thr Asp Ile Tyr Arg Asp Leu His His Tyr Lys Glu
545                 550                 555                 560

Ala Gln Arg Val Ser Gly Phe Leu Ile Leu Ala Ile Glu Ala Pro Ile
                565                 570                 575

Asn Phe Ala Asn Ser Asn Tyr Leu Asn Glu Arg Ile Lys Arg Trp Ile
            580                 585                 590

Glu Glu Glu Ser Phe Glu Gln Asp Lys His Thr Glu Leu His Phe Ile
        595                 600                 605

Ile Leu Asp Leu Ser Ala Val Pro Ala Ile Asp Thr Ser Gly Ile Ala
    610                 615                 620

Phe Leu Ile Asp Ile Lys Lys Ser Ile Glu Lys Arg Gly Leu Glu Leu
625                 630                 635                 640

Val Leu Val Asn Pro Thr Gly Glu Val Met Glu Lys Ile Gln Arg Ala
                645                 650                 655

Asn Glu Ala Glu Asn Tyr Phe Arg Pro Asp Cys Leu Tyr Leu Thr Thr
            660                 665                 670

Gly Glu Ala Ile Ala Ser Leu Ser Ala Leu Ala Lys Met Thr Lys Pro
        675                 680                 685
```

<210> SEQ ID NO 3
<211> LENGTH: 1981
<212> TYPE: DNA
<213> ORGANISM: Zea mays

<400> SEQUENCE: 3

```
gcacgaggag tccgacctga tcgccggcat caccatcgcc agcctcgcca tcccgcaggg     60

catcagctac gccaagctcg ccaacctgcc gcccgtgctc ggactctact cgagcttcgt    120

gccgccgctg gtgtacgcgc tgatggggag ctccaaggac ctggcggtgg ggacggtggc    180

ggtggcgtcg ctgctcatca gctccatgct cggcagcgag gtgtcgccga cggagaaccc    240

cgtgctctac ctgcacctcg ccttcaccgc caccttcttc gccggcgtct tccaggcctc    300

gctcggcctc ctcaggttgg gcttcatcgt ggacctgctg tcgcacgcga cgatcgtggg    360

gttcatggcc ggcgcggcga cggtggtgtg cctgcagcag ctgaagggca tgctgggcct    420

cgtccacttc accacctcca ccgacgtcgt ctccgtcatg gaatccgtct tcagccagac    480

acaccagtgg cggtgggaga gcgtcctgct cggctgcggc ttcctcttct tcctcctcgt    540

cacccgcttc atcagcaaga ggcgtcccaa gctgttctgg atctccgcgg cggcgccgtt    600

gacgtccgtc gtgctcggga gcgttctggt gtacctcacg cacgctgaaa accacggcat    660
```

-continued

```
cgaagtgatc ggttacctga agaaaggcct gaatccaccg tcggtgacaa gcctgcaatt    720

ctcaccgccc tacatgatgc tcgcgctcaa gactgggatc atcaccggcg tcattgccct    780

cgccgaagga atcgccgtgg ggaggagctt cgccatgttc aagaactacc acatgacgga    840

caacaaggag atgatcgcga tcgggacgat gaacgtcctg ggctcgctca cgtcgtgcta    900

cctgaccacg gggcccttct cgcgctccgc cgtgaactac aacgccgggt gcaggacggc    960

catgtcgaac gtggtcatgt cgctggcggt gatggtcacg ctgctgttcc tgacgccgct   1020

gttccactac acgccgctgg tggtgctgtc ggcgatcatc gtctccgcga tgctgggcct   1080

ggtcgacttc ggggccgcgc tgcacctgtg gcgcgtcgac aaggtcgact tctgcgtctg   1140

cgccggcgcg tacctgggcg tcgtcttcgg cagcgtcgag gtcggcctgg tcgtcgccgt   1200

cgccgtctcc ctgctccgcg tcctgctgtt cgtcgcccgg cccaggacca cggtgctcgg   1260

caacatcccc ggcaccatgg tgtaccggag gatggaccag tacgccgccg cgcagacggt   1320

gcccggcgtg ctcgtgctgc gcgtcgacgc gcccgtctac ttcgccaacg ccagctacct   1380

gcgagagagg atctcgcggt ggatcgacga cgaggaggag cgcaccaaga gccagggcga   1440

gatgggcgtg cggtacgttg tcctcgacat gggtgccatc ggtagcatcg acacgagcgg   1500

gacgagcatg ctggacgagc tcaacaagtc cttggacagg aggggaatgc agatcgtgct   1560

ggcgaacccg ggcagcgaga tcatgaagaa gctggacagc tccaaggtgc tggagcagat   1620

cggccacgag tgggtgttcc cgacggtggg cgaggcggtg gcgtcgtgcg actacgtgct   1680

gcactcgcac aagccgggaa tggccaagga cagcgccgcc gcccacgaga gcatggtgtg   1740

acgagcaccg ccacgccaac cgtatgtgta gtgtgctccg gttccggtct gacgtaacca   1800

gtcgtcacgc ggaccgagat gaattatgta tacacgtgtc tcgagtattg tacacctgca   1860

ccgtcgcggg aaaaacgaat tcagagaaga aaggatccca cccggttttt tttggtgaaa   1920

aaaaaaaaaa aaaaaaaaaa aaaaaaaaaa aaaaaaaaaa aaaaaaaaaa aaaaaaaaaa   1980

a                                                                   1981


<210> SEQ ID NO 4
<211> LENGTH: 579
<212> TYPE: PRT
<213> ORGANISM: Zea mays

<400> SEQUENCE: 4

His Glu Glu Ser Asp Leu Ile Ala Gly Ile Thr Ile Ala Ser Leu Ala
  1               5                  10                  15

Ile Pro Gln Gly Ile Ser Tyr Ala Lys Leu Ala Asn Leu Pro Pro Val
             20                  25                  30

Leu Gly Leu Tyr Ser Ser Phe Val Pro Pro Leu Val Tyr Ala Leu Met
         35                  40                  45

Gly Ser Ser Lys Asp Leu Ala Val Gly Thr Val Ala Val Ala Ser Leu
     50                  55                  60

Leu Ile Ser Ser Met Leu Gly Ser Glu Val Ser Pro Thr Glu Asn Pro
 65                  70                  75                  80

Val Leu Tyr Leu His Leu Ala Phe Thr Ala Thr Phe Phe Ala Gly Val
                 85                  90                  95

Phe Gln Ala Ser Leu Gly Leu Leu Arg Leu Gly Phe Ile Val Asp Leu
            100                 105                 110

Leu Ser His Ala Thr Ile Val Gly Phe Met Ala Gly Ala Ala Thr Val
        115                 120                 125

Val Cys Leu Gln Gln Leu Lys Gly Met Leu Gly Leu Val His Phe Thr
```

-continued

```
    130                 135                 140

Thr Ser Thr Asp Val Val Ser Val Met Glu Ser Val Phe Ser Gln Thr
145                 150                 155                 160

His Gln Trp Arg Trp Glu Ser Val Leu Leu Gly Cys Gly Phe Leu Phe
                165                 170                 175

Phe Leu Leu Val Thr Arg Phe Ile Ser Lys Arg Arg Pro Lys Leu Phe
            180                 185                 190

Trp Ile Ser Ala Ala Ala Pro Leu Thr Ser Val Val Leu Gly Ser Val
        195                 200                 205

Leu Val Tyr Leu Thr His Ala Glu Asn His Gly Ile Glu Val Ile Gly
    210                 215                 220

Tyr Leu Lys Lys Gly Leu Asn Pro Pro Ser Val Thr Ser Leu Gln Phe
225                 230                 235                 240

Ser Pro Pro Tyr Met Met Leu Ala Leu Lys Thr Gly Ile Ile Thr Gly
                245                 250                 255

Val Ile Ala Leu Ala Glu Gly Ile Ala Val Gly Arg Ser Phe Ala Met
            260                 265                 270

Phe Lys Asn Tyr His Met Thr Asp Asn Lys Glu Met Ile Ala Ile Gly
        275                 280                 285

Thr Met Asn Val Leu Gly Ser Leu Thr Ser Cys Tyr Leu Thr Thr Gly
    290                 295                 300

Pro Phe Ser Arg Ser Ala Val Asn Tyr Asn Ala Gly Cys Arg Thr Ala
305                 310                 315                 320

Met Ser Asn Val Val Met Ser Leu Ala Val Met Val Thr Leu Leu Phe
                325                 330                 335

Leu Thr Pro Leu Phe His Tyr Thr Pro Leu Val Val Leu Ser Ala Ile
            340                 345                 350

Ile Val Ser Ala Met Leu Gly Leu Val Asp Phe Gly Ala Ala Leu His
        355                 360                 365

Leu Trp Arg Val Asp Lys Val Asp Phe Cys Val Cys Ala Gly Ala Tyr
    370                 375                 380

Leu Gly Val Val Phe Gly Ser Val Glu Val Gly Leu Val Val Ala Val
385                 390                 395                 400

Ala Val Ser Leu Leu Arg Val Leu Leu Phe Val Ala Arg Pro Arg Thr
                405                 410                 415

Thr Val Leu Gly Asn Ile Pro Gly Thr Met Val Tyr Arg Arg Met Asp
            420                 425                 430

Gln Tyr Ala Ala Ala Gln Thr Val Pro Gly Val Leu Val Leu Arg Val
        435                 440                 445

Asp Ala Pro Val Tyr Phe Ala Asn Ala Ser Tyr Leu Arg Glu Arg Ile
    450                 455                 460

Ser Arg Trp Ile Asp Asp Glu Glu Glu Arg Thr Lys Ser Gln Gly Glu
465                 470                 475                 480

Met Gly Val Arg Tyr Val Val Leu Asp Met Gly Ala Ile Gly Ser Ile
                485                 490                 495

Asp Thr Ser Gly Thr Ser Met Leu Asp Glu Leu Asn Lys Ser Leu Asp
            500                 505                 510

Arg Arg Gly Met Gln Ile Val Leu Ala Asn Pro Gly Ser Glu Ile Met
        515                 520                 525

Lys Lys Leu Asp Ser Ser Lys Val Leu Glu Gln Ile Gly His Glu Trp
    530                 535                 540

Val Phe Pro Thr Val Gly Glu Ala Val Ala Ser Cys Asp Tyr Val Leu
545                 550                 555                 560
```

-continued

```
His Ser His Lys Pro Gly Met Ala Lys Asp Ser Ala Ala Ala His Glu
                565                 570                 575

Ser Met Val


<210> SEQ ID NO 5
<211> LENGTH: 1240
<212> TYPE: DNA
<213> ORGANISM: Zea mays

<400> SEQUENCE: 5

gcacgagcct cacggaagct atcgccgttg gccgatcttt cgcctccgta agagggtaca     60

gactcgacgg caacaaggag atgctggcca tggggttctc caacgttgct ggttctctgt    120

cctcgtgcta tgtggcaaca ggttcgttct cccgaacggc agtgaacttc agcgcggggg    180

ccaggtcgac cgtttcaaac atcgtcatgt ccatcaccgt gttcgtcacc ctggagctgt    240

tcatgaagct cctctactac acgcccatgg cggtgctcgc ctccatcatc ctgtcggctc    300

ttccgggact gatcgacatc aaggaggcct gcagcatatg gaagatcgac aagatggatt    360

tcctcacctg cctcggtgcg tttgttggcg tcctgtttgg gtcggtggag attgggcttg    420

cagttgcact tggcatttcc ttcgcaaaga tcatcataca gtcgcttcgg cctcaggtgg    480

agatccttgg caggctacaa gggacagata tcttctgcag cgtcaggcag taccctgtag    540

cctgcctaac tccgactgta ctgcctatac gcgtcgacac atccttcctc tgcttcatca    600

acgccacttc cgtcaaagaa aggatcacag agtgggtttg ggaaggagtg gagacctcaa    660

atggaaaagc gagggagagg atacaagcag ttgtccttga tatgtcaagt gtggtaaaca    720

tcgacacttc aggactcact gcactggaag aaatacacaa ggagttggtg tctcttggct    780

tacagatggc tatagccagt ccgggatgga aggcagttca gaagatgaaa gtgtcacagg    840

tggtggacag ggtaggacag gactggatct tcatgacagt aggtgaagcg gtggaggcct    900

gtctagctgc tcataagggc acagctctcg catgttgagt atgcgttaat tactactatt    960

agtactccta aggataatcc cataagcgat gcggttattt gcatcctatg aaggtgttac   1020

tggaaatgct tacgaaacag aaatgcatgg tttgcacatg atggaggcaa aatacctatg   1080

gtatgacttg actggagtgg tcgtggcgag aaacaaacct gctctgggaa ggacattcct   1140

tgagctccac aaaaacatgt atggtgatat cttgatgatg tgtaactgta cttagtaagt   1200

aaacaagtct ttttgttaaa aaaaaaaaaa aaaaaaaaaa                         1240


<210> SEQ ID NO 6
<211> LENGTH: 311
<212> TYPE: PRT
<213> ORGANISM: Zea mays

<400> SEQUENCE: 6

Thr Ser Leu Thr Glu Ala Ile Ala Val Gly Arg Ser Phe Ala Ser Val
  1               5                  10                  15

Arg Gly Tyr Arg Leu Asp Gly Asn Lys Glu Met Leu Ala Met Gly Phe
             20                  25                  30

Ser Asn Val Ala Gly Ser Leu Ser Ser Cys Tyr Val Ala Thr Gly Ser
         35                  40                  45

Phe Ser Arg Thr Ala Val Asn Phe Ser Ala Gly Ala Arg Ser Thr Val
     50                  55                  60

Ser Asn Ile Val Met Ser Ile Thr Val Phe Val Thr Leu Glu Leu Phe
 65                  70                  75                  80
```

-continued

```
Met Lys Leu Leu Tyr Tyr Thr Pro Met Ala Val Leu Ala Ser Ile Ile
                85                  90                  95

Leu Ser Ala Leu Pro Gly Leu Ile Asp Ile Lys Glu Ala Cys Ser Ile
            100                 105                 110

Trp Lys Ile Asp Lys Met Asp Phe Leu Thr Cys Leu Gly Ala Phe Val
        115                 120                 125

Gly Val Leu Phe Gly Ser Val Glu Ile Gly Leu Ala Val Ala Leu Gly
    130                 135                 140

Ile Ser Phe Ala Lys Ile Ile Ile Gln Ser Leu Arg Pro Gln Val Glu
145                 150                 155                 160

Ile Leu Gly Arg Leu Gln Gly Thr Asp Ile Phe Cys Ser Val Arg Gln
                165                 170                 175

Tyr Pro Val Ala Cys Leu Thr Pro Thr Val Leu Pro Ile Arg Val Asp
            180                 185                 190

Thr Ser Phe Leu Cys Phe Ile Asn Ala Thr Ser Val Lys Glu Arg Ile
        195                 200                 205

Thr Glu Trp Val Trp Glu Gly Val Glu Thr Ser Asn Gly Lys Ala Arg
    210                 215                 220

Glu Arg Ile Gln Ala Val Val Leu Asp Met Ser Ser Val Val Asn Ile
225                 230                 235                 240

Asp Thr Ser Gly Leu Thr Ala Leu Glu Glu Ile His Lys Glu Leu Val
                245                 250                 255

Ser Leu Gly Leu Gln Met Ala Ile Ala Ser Pro Gly Trp Lys Ala Val
            260                 265                 270

Gln Lys Met Lys Val Ser Gln Val Val Asp Arg Val Gly Gln Asp Trp
        275                 280                 285

Ile Phe Met Thr Val Gly Glu Ala Val Glu Ala Cys Leu Ala Ala His
    290                 295                 300

Lys Gly Thr Ala Leu Ala Cys
305                 310
```

<210> SEQ ID NO 7
<211> LENGTH: 780
<212> TYPE: DNA
<213> ORGANISM: Helianthus tuberosus

<400> SEQUENCE: 7

```
ttcggcacga gctcgtgccg cgattcacct ctggacacta gacaaattcg actttgttgt     60

atgcatgagt gcatactttg gtgttgtctt tgggagtgtt gaaattggat tagttatcgc    120

ggtcgcattg tcgttgctta gggtactcct atttgtctcg aggccaagaa catcgacgct    180

aggtctcata cccgattcca ctatttatag aagtatggat caataccaaa atgcgaaaag    240

cgttccagga atcttgatac ttcaaatcga agcacctatt tactttgcta actctagcta    300

cttgagggaa aggattgtga gatgggttga tgaagaggaa gataggttga agtctttaaa    360

ggagaatgac ttgcaatatg tcattcttgc attgagtgct gttggaaata ttgatacaag    420

tgggataaca atgcttggag aagttaaaaa ggttatggaa agaagagggc taaagttggt    480

tttagcgaat ccgggcggag aggtaataaa gaagatgaac aaagcgaagt tgatagaggt    540

gatcgggcaa gaatggatat atctaacagt gggagaagcg gttggagcgt gcaactttat    600

gcttcatact tacaagaacg ccgaaaagcc aacttctgga tcagaatcag gaaaagagag    660

tcgaaacgac aataatgtct agttggatgt tgttatttga tcatttgaca gcatttttcg    720

tcgaaggcgt attcttaatg ataaataatt tgtatattga ttaaaaaaaa aaaaaaaaaa    780
```

-continued

<210> SEQ ID NO 8
<211> LENGTH: 226
<212> TYPE: PRT
<213> ORGANISM: Helianthus tuberosus

<400> SEQUENCE: 8

```
Ser Ala Arg Ala Arg Ala Ala Ile His Leu Trp Thr Leu Asp Lys Phe
  1               5                  10                  15

Asp Phe Val Val Cys Met Ser Ala Tyr Phe Gly Val Val Phe Gly Ser
             20                  25                  30

Val Glu Ile Gly Leu Val Ile Ala Val Ala Leu Ser Leu Leu Arg Val
         35                  40                  45

Leu Leu Phe Val Ser Arg Pro Arg Thr Ser Thr Leu Gly Leu Ile Pro
     50                  55                  60

Asp Ser Thr Ile Tyr Arg Ser Met Asp Gln Tyr Gln Asn Ala Lys Ser
 65                  70                  75                  80

Val Pro Gly Ile Leu Ile Leu Gln Ile Glu Ala Pro Ile Tyr Phe Ala
                 85                  90                  95

Asn Ser Ser Tyr Leu Arg Glu Arg Ile Val Arg Trp Val Asp Glu Glu
            100                 105                 110

Glu Asp Arg Leu Lys Ser Leu Lys Glu Asn Asp Leu Gln Tyr Val Ile
        115                 120                 125

Leu Ala Leu Ser Ala Val Gly Asn Ile Asp Thr Ser Gly Ile Thr Met
    130                 135                 140

Leu Gly Glu Val Lys Lys Val Met Glu Arg Arg Gly Leu Lys Leu Val
145                 150                 155                 160

Leu Ala Asn Pro Gly Gly Glu Val Ile Lys Lys Met Asn Lys Ala Lys
                165                 170                 175

Leu Ile Glu Val Ile Gly Gln Glu Trp Ile Tyr Leu Thr Val Gly Glu
            180                 185                 190

Ala Val Gly Ala Cys Asn Phe Met Leu His Thr Tyr Lys Asn Ala Glu
        195                 200                 205

Lys Pro Thr Ser Gly Ser Glu Ser Gly Lys Glu Ser Arg Asn Asp Asn
    210                 215                 220

Asn Val
225
```

<210> SEQ ID NO 9
<211> LENGTH: 484
<212> TYPE: DNA
<213> ORGANISM: Oryza sativa
<220> FEATURE:
<221> NAME/KEY: unsure
<222> LOCATION: (398)
<223> OTHER INFORMATION: n = A, C, G or T
<220> FEATURE:
<221> NAME/KEY: unsure
<222> LOCATION: (483)
<223> OTHER INFORMATION: n = A, C, G or T

<400> SEQUENCE: 9

```
cttacaggca tcaagagctt tacaaagaaa accgatataa tttccgtgat gagctgaagt     60

ccaaacagag cgcataacag gtggaattgg caaactattg tgattggcat aactttcctt    120

gcattccttc tgcttgccaa gtacattgga aagaagaata ggaagttctt ctgggtgcca    180

gctattgctc ctataacttc agttattttg gcaacccttt ttgtgttcat tactcgtgct    240

gacaagcaag gtgttcagat tgttaaccac atcaaaaagg gcataaaccc atcatcagtc    300
```

-continued cacaaaattt atttcactgg tccatttgtt gcaaaaggtt tcaagatcgg tgtcatttcc 360
gccatgatcg gtttaacgga agctgtggca attgggganga cgtttgctgc tctgaaggac 420
tatcaattag attggaacaa ggagatggaa cacttggaac tatgaacata caaggtcaat 480 gana 484

<210> SEQ ID NO 10
<211> LENGTH: 147
<212> TYPE: PRT
<213> ORGANISM: Oryza sativa
<220> FEATURE:
<221> NAME/KEY: UNSURE
<222> LOCATION: (17)
<223> OTHER INFORMATION: Xaa = any amino acid
<220> FEATURE:
<221> NAME/KEY: UNSURE
<222> LOCATION: (131)
<223> OTHER INFORMATION: Xaa = any amino acid

<400> SEQUENCE: 10

Gly Ile Lys Ser Phe Thr Lys Lys Thr Asp Ile Ile Ser Val Met Ser
1 5 10 15

Xaa Ser Pro Asn Arg Ala His Asn Arg Trp Asn Trp Gln Thr Ile Val
20 25 30

Ile Gly Ile Thr Phe Leu Ala Phe Leu Leu Leu Ala Lys Tyr Ile Gly
35 40 45

Lys Lys Asn Arg Lys Phe Phe Trp Val Pro Ala Ile Ala Pro Ile Thr
50 55 60

Ser Val Ile Leu Ala Thr Leu Phe Val Phe Ile Thr Arg Ala Asp Lys
65 70 75 80

Gln Gly Val Gln Ile Val Asn His Ile Lys Lys Gly Ile Asn Pro Ser
85 90 95

Ser Val His Lys Ile Tyr Phe Thr Gly Pro Phe Val Ala Lys Gly Phe
100 105 110

Lys Ile Gly Val Ile Ser Ala Met Ile Gly Leu Thr Glu Ala Val Ala
115 120 125

Ile Gly Xaa Thr Phe Ala Ala Leu Lys Asp Tyr Gln Leu Asp Trp Asn
130 135 140

Lys Glu Met
145

<210> SEQ ID NO 11
<211> LENGTH: 510
<212> TYPE: DNA
<213> ORGANISM: Oryza sativa

<400> SEQUENCE: 11
gcacgagatc actcgcagtt aagattagtt aatccaagct ctagctcgat cgcgcggtcg 60
ccggagctga ggtagacgaa ggagtgcgac gagctaagat gggtagtgga agcgcggcga 120
acggcggcgg aggaggggcg ggggcggcga gggtgccgat gccggcggcg aagccgttcc 180
tggagacgct ggggggggaac atgaaggaga cattcctgcc ggacgacccg ttcagggtgg 240
tgcggcggga gcgcgggtgc gggcggcgcg cggcggcggc gctccggtac gtgttcccgt 300
tcatggagtg ggcgccgtcg tacaccctcg gcaccctcaa gtccgacctc atcgccggca 360
caccattgcc agcctcagca tcccgcaagg gatcagctag ccaagctcgc aactccctcg 420
cgtcctcggc tcaaatcaac ttcgtgcccc gcggtgtacc gatgaggggga ctcgagggac 480 tgcggtagga cgtggcgtgg cgtcctgcga 510

-continued

<210> SEQ ID NO 12
<211> LENGTH: 98
<212> TYPE: PRT
<213> ORGANISM: Oryza sativa

<400> SEQUENCE: 12

```
Met Gly Ser Gly Ser Ala Ala Asn Gly Gly Gly Gly Gly Ala Gly Ala
  1               5                  10                  15

Ala Arg Val Pro Met Pro Ala Ala Lys Pro Phe Leu Glu Thr Leu Gly
             20                  25                  30

Gly Asn Met Lys Glu Thr Phe Leu Pro Asp Asp Pro Phe Arg Val Val
         35                  40                  45

Arg Arg Glu Arg Gly Cys Gly Arg Arg Ala Ala Ala Ala Leu Arg Tyr
     50                  55                  60

Val Phe Pro Phe Met Glu Trp Ala Pro Ser Tyr Thr Leu Gly Thr Leu
 65                  70                  75                  80

Lys Ser Asp Leu Ile Ala Gly Thr Pro Leu Pro Ala Ser Ala Ser Arg
                 85                  90                  95

Lys Gly
```

<210> SEQ ID NO 13
<211> LENGTH: 493
<212> TYPE: DNA
<213> ORGANISM: Oryza sativa

<400> SEQUENCE: 13

```
acgacatgac ccgtggcacc cgggcaactt cctcatcgga tgctccttcc tcatattcat     60

cctcaccaca cggttcatcg ggaggaggta caagaagctg ttctggctgt cagcgatctc    120

gcctctgctg tcggtcatcc tgtccaccgc tgcggtctac gcgacaaggg ctgacaggca    180

cggcgtcaag atcatccaga aggtgcacgc gggcctaaac ccaagctccg tggaagcaga    240

tacacctcaa cgggccgcac acaacggagt gcgcccaaga tcgccgtcat ctgcgcatca    300

tcgccctcac ggaagctatc gccgttggcc gatctttcgc ctccgtaaga gggtacagac    360

tcgacggcaa caaggagatg ctggccatgg ggttctccaa cgttgctggt tctctgtcct    420

cgtgctatgt ggcaacaggt tcgttctccc gaacggcagt gaacttcagc ggcgggggcc    480

agtcgaccgt ttc                                                       493
```

<210> SEQ ID NO 14
<211> LENGTH: 159
<212> TYPE: PRT
<213> ORGANISM: Oryza sativa
<220> FEATURE:
<221> NAME/KEY: UNSURE
<222> LOCATION: (74)
<223> OTHER INFORMATION: Xaa = any amino acid

<400> SEQUENCE: 14

```
Trp His Pro Gly Asn Phe Leu Ile Gly Cys Ser Phe Leu Ile Phe Ile
  1               5                  10                  15

Leu Thr Thr Arg Phe Ile Gly Arg Arg Tyr Lys Lys Leu Phe Trp Leu
             20                  25                  30

Ser Ala Ile Ser Pro Leu Leu Ser Val Ile Leu Ser Thr Ala Ala Val
         35                  40                  45

Tyr Ala Thr Arg Ala Asp Arg His Gly Val Lys Ile Ile Gln Lys Val
     50                  55                  60
```

-continued

```
His Ala Gly Leu Asn Pro Ser Ser Val Xaa Gln Ile His Leu Asn Gly
 65                  70                  75                  80

Pro His Thr Thr Glu Cys Ala Gln Asp Arg Arg His Leu Arg Ile Ile
                 85                  90                  95

Ala Leu Thr Glu Ala Ile Ala Val Gly Arg Ser Phe Ala Ser Val Arg
            100                 105                 110

Gly Tyr Arg Leu Asp Gly Asn Lys Glu Met Leu Ala Met Gly Phe Ser
        115                 120                 125

Asn Val Ala Gly Ser Leu Ser Ser Cys Tyr Val Ala Thr Gly Ser Phe
    130                 135                 140

Ser Arg Thr Ala Val Asn Phe Ser Gly Gly Gly Gln Ser Thr Val
145                 150                 155


<210> SEQ ID NO 15
<211> LENGTH: 2067
<212> TYPE: DNA
<213> ORGANISM: Glycine max

<400> SEQUENCE: 15

gcacgagcca caccagacca cactccacaa acttaggcac agagtctccg aaatcttctt     60

tcccagatgac cctctccacc gtttcaagaa ccaaactcgc tttaaaaagt tcctcctcgc   120

acttcagtat ctcttcccca ttttcgactg ggccccaaac tacaatctta cccttctccg    180

ctctgacctc atctctggcc tcaccattgc cagcctcgcc attcctcagg gaatcagtta    240

tgccaagctt gccaacttgc cacctattct tggattatat tcgagttttg ttcccccatt    300

gatatactcg ctgcttggaa gttctagaca tcttggtgtt ggacctgttt ccattgcgtc    360

tttggtcatg ggatcaatgt taagtgataa aatttcttac actcaagaac ctattctcta    420

tctgggattg gctttcaccg ccactttctt tgctggtgta ttccaagctt ctctgggtat    480

attaaggcta ggcttcgtaa ttgattttct gtcgaaggca acgctggttg gattcacagg    540

cggtgctgcc attattgtgt cactgcagca gctgaaaggt ttacttggaa tagtgcactt    600

taccagcaag atgcaaataa ttccagtaac gatctctgtt ttcaagcaaa gacacgagtg    660

gtcatggcaa accattcttt tgggattcgg cttcctggtc ttcttgctga caacaaggca    720

cattagtttg aggaaaccaa aactattctg ggtttcagca gctgccccat tgacatcagt    780

tattctgtca accattttag tctttcttct gagaaataag actcatcaaa tttcagttat    840

tgggcactta ccaaagggag ttaatccacc atcagcaaac atgttatact tcaatggtcc    900

ttacttgggt cttgctatca aaactggcat catcacaggg atcttatctc tcactgaagg    960

aattgcagta gggagaacat ttgcttcact taagaactac caggtggatg gaaacaaaga   1020

aatgatggcc attggtctaa tgaacatagc tggctcgtgt tcttcatgtt atgttacaac   1080

gggatccttt tctcgatcgg ctgttaacta taatgctgga gcacagacaa cagtttcaaa   1140

tataatcatg gctgcagctg ttctagtgac acttctgttt ctcatgcctc ttttctacta   1200

tacaccaaat gttgtcttag cggccattat catcactgct gtgattggtc taatagatta   1260

tcaatctgca tataaattgt ggaaggttga caaacttgat ttcttggcct gtttgtgctc   1320

ctttttttggg gttctgttca tttcagtgcc tttaggtctt ggtatagcgg ttatcatatc   1380

agtcctcaag atcctgcttc atgtcactcg accaaacact ttggttttgg ggaatatacc   1440

aggaacacaa atattccaca acataaacca atacaaaaaa gctttaagag ttccttcatt   1500

tctcattttg gctgttgagt ctccaatcta ttttgctaac tcaacttatc ttcaagaaag   1560

gatactgaga tgggttcgag aagaggaaga gcatataaaa gctaataatg gagctccatt   1620
```

-continued gaagtgcata attttagaca tgacagctgt cacagccaca gacacaagtg ggcttgacac 1680
tttatgtgaa cttagaaaga tgctggagaa gagatcactt gagtttgtgc tggcaaatcc 1740
tgttggaaat gtgatggaaa aattgcataa gtcaaacatt ttggattctt ttggattaaa 1800
aggagtctat ctcacagtgg gagaagctgt gactgacatt tcatcaatct ggaaagctca 1860
gccttgattt cccatcaatg ttgttcaagg acttatatat ggggataaac tctctaacct 1920
tatatttttg cctgcgatga atacttttgt ttaaattccg gagagtctaa tttctgttag 1980
tagaaacctt caaaacaata ttaccccgta aaaatgaaaa aggagtgcct tcaaaatcaa 2040
aaaaaaaaaa aaaaaaaaaa aaaaaaa 2067

<210> SEQ ID NO 16
<211> LENGTH: 621
<212> TYPE: PRT
<213> ORGANISM: Glycine max

<400> SEQUENCE: 16

His Glu Pro His Gln Thr Thr Leu His Lys Leu Arg His Arg Val Ser
1 5 10 15

Glu Ile Phe Phe Pro Asp Asp Pro Leu His Arg Phe Lys Asn Gln Thr
20 25 30

Arg Phe Lys Lys Phe Leu Leu Ala Leu Gln Tyr Leu Phe Pro Ile Phe
35 40 45

Asp Trp Ala Pro Asn Tyr Asn Leu Thr Leu Leu Arg Ser Asp Leu Ile
50 55 60

Ser Gly Leu Thr Ile Ala Ser Leu Ala Ile Pro Gln Gly Ile Ser Tyr
65 70 75 80

Ala Lys Leu Ala Asn Leu Pro Pro Ile Leu Gly Leu Tyr Ser Ser Phe
85 90 95

Val Pro Pro Leu Ile Tyr Ser Leu Leu Gly Ser Ser Arg His Leu Gly
100 105 110

Val Gly Pro Val Ser Ile Ala Ser Leu Val Met Gly Ser Met Leu Ser
115 120 125

Asp Lys Ile Ser Tyr Thr Gln Glu Pro Ile Leu Tyr Leu Gly Leu Ala
130 135 140

Phe Thr Ala Thr Phe Phe Ala Gly Val Phe Gln Ala Ser Leu Gly Ile
145 150 155 160

Leu Arg Leu Gly Phe Val Ile Asp Phe Leu Ser Lys Ala Thr Leu Val
165 170 175

Gly Phe Thr Gly Gly Ala Ala Ile Ile Val Ser Leu Gln Gln Leu Lys
180 185 190

Gly Leu Leu Gly Ile Val His Phe Thr Ser Lys Met Gln Ile Ile Pro
195 200 205

Val Thr Ile Ser Val Phe Lys Gln Arg His Glu Trp Ser Trp Gln Thr
210 215 220

Ile Leu Leu Gly Phe Gly Phe Leu Val Phe Leu Leu Thr Thr Arg His
225 230 235 240

Ile Ser Leu Arg Lys Pro Lys Leu Phe Trp Val Ser Ala Ala Ala Pro
245 250 255

Leu Thr Ser Val Ile Leu Ser Thr Ile Leu Val Phe Leu Leu Arg Asn
260 265 270

Lys Thr His Gln Ile Ser Val Ile Gly His Leu Pro Lys Gly Val Asn
275 280 285

-continued

```
Pro Pro Ser Ala Asn Met Leu Tyr Phe Asn Gly Pro Tyr Leu Gly Leu
    290                 295                 300

Ala Ile Lys Thr Gly Ile Ile Thr Gly Ile Leu Ser Leu Thr Glu Gly
305                 310                 315                 320

Ile Ala Val Gly Arg Thr Phe Ala Ser Leu Lys Asn Tyr Gln Val Asp
                325                 330                 335

Gly Asn Lys Glu Met Met Ala Ile Gly Leu Met Asn Ile Ala Gly Ser
            340                 345                 350

Cys Ser Ser Cys Tyr Val Thr Thr Gly Ser Phe Ser Arg Ser Ala Val
        355                 360                 365

Asn Tyr Asn Ala Gly Ala Gln Thr Thr Val Ser Asn Ile Ile Met Ala
    370                 375                 380

Ala Ala Val Leu Val Thr Leu Leu Phe Leu Met Pro Leu Phe Tyr Tyr
385                 390                 395                 400

Thr Pro Asn Val Val Leu Ala Ala Ile Ile Ile Thr Ala Val Ile Gly
                405                 410                 415

Leu Ile Asp Tyr Gln Ser Ala Tyr Lys Leu Trp Lys Val Asp Lys Leu
            420                 425                 430

Asp Phe Leu Ala Cys Leu Cys Ser Phe Phe Gly Val Leu Phe Ile Ser
        435                 440                 445

Val Pro Leu Gly Leu Gly Ile Ala Val Ile Ile Ser Val Leu Lys Ile
    450                 455                 460

Leu Leu His Val Thr Arg Pro Asn Thr Leu Val Leu Gly Asn Ile Pro
465                 470                 475                 480

Gly Thr Gln Ile Phe His Asn Ile Asn Gln Tyr Lys Lys Ala Leu Arg
                485                 490                 495

Val Pro Ser Phe Leu Ile Leu Ala Val Glu Ser Pro Ile Tyr Phe Ala
            500                 505                 510

Asn Ser Thr Tyr Leu Gln Glu Arg Ile Leu Arg Trp Val Arg Glu Glu
        515                 520                 525

Glu Glu His Ile Lys Ala Asn Asn Gly Ala Pro Leu Lys Cys Ile Ile
    530                 535                 540

Leu Asp Met Thr Ala Val Thr Ala Thr Asp Thr Ser Gly Leu Asp Thr
545                 550                 555                 560

Leu Cys Glu Leu Arg Lys Met Leu Glu Lys Arg Ser Leu Glu Phe Val
                565                 570                 575

Leu Ala Asn Pro Val Gly Asn Val Met Glu Lys Leu His Lys Ser Asn
            580                 585                 590

Ile Leu Asp Ser Phe Gly Leu Lys Gly Val Tyr Leu Thr Val Gly Glu
        595                 600                 605

Ala Val Thr Asp Ile Ser Ser Ile Trp Lys Ala Gln Pro
    610                 615                 620


<210> SEQ ID NO 17
<211> LENGTH: 2449
<212> TYPE: DNA
<213> ORGANISM: Glycine max

<400> SEQUENCE: 17

gcacgagcta gctcgcacat taagttatat aacacatatt tgcttgctta gaaatactat     60

tattgaagat atggggagtg tagattatga gtaccctttg ggcatgaaca actttgagag    120

agtgcaccaa gtcgaggttc caccgccaca gccgtttttc aagtctctaa agtactcttt    180

gaaggagact ttcttccctg atgacccttt gaggcagttc aagaacaagc cagcttccaa    240
```

-continued

```
gaagttcatg cttggccttc agttcttctt ccccattttc gaatgggctc ccaaatacac    300

ctttcagttc ttgaaagctg acctcatagc tggcatcacc atcgctagct tggccattcc    360

tcagggcatc agttatgcca agctcgccaa cctccctcca attcttggac tatattcgag    420

ctttatacca ccattgattt atgcgatgat gggtagctcg agggatttgg cagtggggac    480

tgtggcggtt ggatcgcttc tgatgggttc gatgttgagt aatgccgttg atcccaatga    540

agacccaaag ctttacctcc acctggcttt cacagctaca ttatttgctg gtgtttttca    600

ggctgccttg ggtctgttta ggttggggtt gatcgtggat ttctctgtcac atgcaaccat    660

aatagggttc atgggaggag cagccacggt ggtgtgtctg cagcaactaa aatcgattct    720

tggccttgag catttcaccc atggagctga tatcatatca gtgatgcgct ctgttttcac    780

ccaaactcat gagtggaggt gggaaagtgc tgtgttagga tgtgtcttca ttttcttcct    840

ccttagcaca agatacttca gcaaaaaacg accaaggttt ttttgggtgt cagcaatggc    900

gccattgacg tccgttatat tgggaagtct cttggtttat ttcactcacg ccgagaagca    960

cggtgttgaa gtgataggag aactgaagaa gggtttgaat ccaccatcac tcacaaatct   1020

ggtatttgtg tcgccttaca tgactacagc tgtcaaaact ggcattgtcg ttggcatcat   1080

atcacttgcg gaaggaatag cagtaggaag aagctttgca atgtataaaa attacaatat   1140

tgatggcaac aaagagatga tagctattgg gaccatgaac gtagttggtt ctttcacctc   1200

ttgctacctc acaacaggac cattttcgcg ttcggctgtg aactataacg ctggatgcaa   1260

gacagcagct tccaacatta taatgtcact tgcagtaatg ttgacattgt tattcctgac   1320

acccttgttc cattacactc ccctggtggt gctatcagct attatcgtat ctgcaatgct   1380

tggactcata gattatgaag cagccatcca tctatttaag gttgacaaat ttgactttgt   1440

ggtgtgcatg agtgcataca ttggcgtggt ctttggcagt gttgaaattg gcttagtcat   1500

agctattgta atatctgtac ttcgggtact tctatttatt gcaaggccaa ggacattcgt   1560

tttgggcaac attccaaatt ctgtgatata ccgaaatgtt gagcactatc aaaatgcaaa   1620

acatgttcct ggaatgctaa ttctagagat tgatgcacca atttactttg ccaatgccag   1680

ctatttaaga gaaaggatca caaggtggat tgatgaagaa gaagaaagaa ttaaagctac   1740

aggggagact agtttgcagt atgttataat tgatatgagt gctgttggaa acattgatac   1800

aagtggaata agtatgcttg aagaggtgaa gaagattaca gagagaagag agctacagct   1860

tgttttggtc aatcctgtaa gtgaagtgat gaagaaactg aacaaatcga agttccaaaa   1920

tcatttaggg aagaaatgga tctatctgac tgttgaagag gccgttggag catgcaactt   1980

caatctacgt gcaagcaaaa cgaacccaaa gaaagatgaa acagagggtt ggaacaatgt   2040

gtgactgagt catatgccaa agagtattct aaataactca aaaagcttat tcgttttcgt   2100

cttagtaatg ttaccactac aatgtgtggc atgagaattt ctgaatcacg ccgaagaagt   2160

tttaaaggca taggaaaatg aaagatgcaa gggtcttcta atttctcaac tctgcatcct   2220

tagttagaag aaaatctcct atgtataggc tgttgaaata atctttacgt atcatgcttg   2280

ataatatatt caagagaaat gctagcaaca cactctcaga cacactcttt tgaacacatg   2340

taaagaggta aagaagtgtg ttgctagcac tcctccatat tcaattgtaa agtaattgcc   2400

atgagaattt aaaaatcctt tggaaaaaaa aaaaaaaaaa aaaaaaaaa               2449
```

<210> SEQ ID NO 18
<211> LENGTH: 680
<212> TYPE: PRT
<213> ORGANISM: Glycine max -continued

```
<400> SEQUENCE: 18

His Glu Leu Ala Arg Thr Leu Ser Tyr Ile Thr His Ile Cys Leu Leu
  1               5                  10                  15

Arg Asn Thr Ile Ile Glu Asp Met Gly Ser Val Asp Tyr Glu Tyr Pro
             20                  25                  30

Leu Gly Met Asn Asn Phe Glu Arg Val His Gln Val Glu Val Pro Pro
         35                  40                  45

Pro Gln Pro Phe Phe Lys Ser Leu Lys Tyr Ser Leu Lys Glu Thr Phe
     50                  55                  60

Phe Pro Asp Asp Pro Leu Arg Gln Phe Lys Asn Lys Pro Ala Ser Lys
 65                  70                  75                  80

Lys Phe Met Leu Gly Leu Gln Phe Phe Phe Pro Ile Phe Glu Trp Ala
                 85                  90                  95

Pro Lys Tyr Thr Phe Gln Phe Leu Lys Ala Asp Leu Ile Ala Gly Ile
            100                 105                 110

Thr Ile Ala Ser Leu Ala Ile Pro Gln Gly Ile Ser Tyr Ala Lys Leu
        115                 120                 125

Ala Asn Leu Pro Pro Ile Leu Gly Leu Tyr Ser Ser Phe Ile Pro Pro
    130                 135                 140

Leu Ile Tyr Ala Met Met Gly Ser Ser Arg Asp Leu Ala Val Gly Thr
145                 150                 155                 160

Val Ala Val Gly Ser Leu Leu Met Gly Ser Met Leu Ser Asn Ala Val
                165                 170                 175

Asp Pro Asn Glu Asp Pro Lys Leu Tyr Leu His Leu Ala Phe Thr Ala
            180                 185                 190

Thr Leu Phe Ala Gly Val Phe Gln Ala Ala Leu Gly Leu Phe Arg Leu
        195                 200                 205

Gly Leu Ile Val Asp Phe Leu Ser His Ala Thr Ile Ile Gly Phe Met
    210                 215                 220

Gly Gly Ala Ala Thr Val Val Cys Leu Gln Gln Leu Lys Ser Ile Leu
225                 230                 235                 240

Gly Leu Glu His Phe Thr His Gly Ala Asp Ile Ile Ser Val Met Arg
                245                 250                 255

Ser Val Phe Thr Gln Thr His Glu Trp Arg Trp Glu Ser Ala Val Leu
            260                 265                 270

Gly Cys Val Phe Ile Phe Phe Leu Leu Ser Thr Arg Tyr Phe Ser Lys
        275                 280                 285

Lys Arg Pro Arg Phe Phe Trp Val Ser Ala Met Ala Pro Leu Thr Ser
    290                 295                 300

Val Ile Leu Gly Ser Leu Leu Val Tyr Phe Thr His Ala Glu Lys His
305                 310                 315                 320

Gly Val Glu Val Ile Gly Glu Leu Lys Lys Gly Leu Asn Pro Pro Ser
                325                 330                 335

Leu Thr Asn Leu Val Phe Val Ser Pro Tyr Met Thr Thr Ala Val Lys
            340                 345                 350

Thr Gly Ile Val Val Gly Ile Ile Ser Leu Ala Glu Gly Ile Ala Val
        355                 360                 365

Gly Arg Ser Phe Ala Met Tyr Lys Asn Tyr Asn Ile Asp Gly Asn Lys
    370                 375                 380

Glu Met Ile Ala Ile Gly Thr Met Asn Val Val Gly Ser Phe Thr Ser
385                 390                 395                 400

Cys Tyr Leu Thr Thr Gly Pro Phe Ser Arg Ser Ala Val Asn Tyr Asn
```

-continued

```
                405                 410                 415

Ala Gly Cys Lys Thr Ala Ala Ser Asn Ile Ile Met Ser Leu Ala Val
            420                 425                 430

Met Leu Thr Leu Leu Phe Leu Thr Pro Leu Phe His Tyr Thr Pro Leu
        435                 440                 445

Val Val Leu Ser Ala Ile Ile Val Ser Ala Met Leu Gly Leu Ile Asp
    450                 455                 460

Tyr Glu Ala Ala Ile His Leu Phe Lys Val Asp Lys Phe Asp Phe Val
465                 470                 475                 480

Val Cys Met Ser Ala Tyr Ile Gly Val Val Phe Gly Ser Val Glu Ile
                485                 490                 495

Gly Leu Val Ile Ala Ile Val Ile Ser Val Leu Arg Val Leu Leu Phe
            500                 505                 510

Ile Ala Arg Pro Arg Thr Phe Val Leu Gly Asn Ile Pro Asn Ser Val
        515                 520                 525

Ile Tyr Arg Asn Val Glu His Tyr Gln Asn Ala Lys His Val Pro Gly
    530                 535                 540

Met Leu Ile Leu Glu Ile Asp Ala Pro Ile Tyr Phe Ala Asn Ala Ser
545                 550                 555                 560

Tyr Leu Arg Glu Arg Ile Thr Arg Trp Ile Asp Glu Glu Glu Glu Arg
                565                 570                 575

Ile Lys Ala Thr Gly Glu Thr Ser Leu Gln Tyr Val Ile Ile Asp Met
            580                 585                 590

Ser Ala Val Gly Asn Ile Asp Thr Ser Gly Ile Ser Met Leu Glu Glu
        595                 600                 605

Val Lys Lys Ile Thr Glu Arg Arg Glu Leu Gln Leu Val Leu Val Asn
    610                 615                 620

Pro Val Ser Glu Val Met Lys Lys Leu Asn Lys Ser Lys Phe Gln Asn
625                 630                 635                 640

His Leu Gly Lys Lys Trp Ile Tyr Leu Thr Val Glu Glu Ala Val Gly
                645                 650                 655

Ala Cys Asn Phe Asn Leu Arg Ala Ser Lys Thr Asn Pro Lys Lys Asp
            660                 665                 670

Glu Thr Glu Gly Trp Asn Asn Val
        675                 680


<210> SEQ ID NO 19
<211> LENGTH: 2311
<212> TYPE: DNA
<213> ORGANISM: Triticum aestivum

<400> SEQUENCE: 19

gcacgagggc cggtgaaccc tgagcgcgcg gcggctccat ccaccgatca caggaaccac      60

cgtatatccg gataacaaaa atttgttcca gtagcagaga tggttcatca tatatctgac     120

gaggcagcag atgaacctag catcaccaca cagacacccc ccaatgaccc atctcaagca     180

ccgctggtgt acaaagtggg ctatccccct ccgaagaact tggccacaga gtttacagaa     240

acattgaggg agactttctt ccacgacaac ccgctgcgtc agtataaggg ccaatccgga     300

ccgaggaggt tcatgatggg gctggagttc ttgtttccta tatttgggtg ggtagggat      360

tacagtctca acaagttcaa aggcgatctg attgccggat tgaccatcgc aagtctctgt     420

attcctcagg acattggcta ttcgaagctt gctaatctgg atccgcagta tgggctttac     480

tccagcttca ttcctccatt gatctatgct gcaatgggta gctcaaggga tatagcgatt     540
```

-continued

```
ggtccagttg ctgtggtttc tcttttgata ggttcacttc tacaagctga ggttgaccat    600

gtcaaaaaca aggaggaata catgcgcctc gctttcacgg caaccttctt cgctggtatc    660

actcaagcag ccttaggatt tctaaggtta ggattcctta tagagttctt gtcgcatgct    720

gcgattgtcg gattcatggg gggagctgcc attactattg ccctgcagca gctgaaatac    780

gtgttgggca tcgcaaactt tacaaggaaa accgacatag tttctgtcat ggaatctgtc    840

tggagatcag ttcatcacgg gtggaactgg cagacaattg tgattggcgt atctttcctg    900

gttttccttc tgtttgcgaa gtacatcgga aagaagaaaa ggaagctttt ctgggtgcca    960

gctattgctc ctataatttc agtgattcta gcaacatttt ttgtatacat tactcgtgcc   1020

gacaagcaag gagttcagat agtgaagcac attgaacagg gaatcaaccc atcatcagta   1080

cacaagattt atttcaccgg cccatttgtt gcaaaaggtt tcaagatcgg tgttgtttgc   1140

ggcatagttg gtttgacaga agctgtagct attggaagga catttgctgc tatgaaggac   1200

taccagttag atggaaacaa ggagatggta gcacttggaa ccatgaacat agtaggctca   1260

atgacatctt gctatgtcac aacaggttct ttctcacgtt cggcagttaa cttcatggct   1320

ggctgcaaga ctcctgtatc caatgtggtt atgtcagtag tggttcttct taccttgttg   1380

gtcatcacac cgctattcaa atatacaccg aatgcaatcc tagggtcgat cattatttct   1440

gcggtgatcg gccttgtgga ctacgaagca gcaattctca tctggaaagt tgacaaattg   1500

gacttcattg cttgcatggg agcttttttc ggtgttgttt ttgtatccgt tgagattggc   1560

ctcttgattg ctgtagcaat ctcatttgcc aaaatacttc ttcaagtaac aaggccaagg   1620

acagccctac ttggaaacct tcccggcacc actatatacc ggaacatcag ccagtatcca   1680

gaagcaaaac ttactcctgg ggtggtgatt gtgagggttg attctgctat ttatttttcc   1740

aactctaatt acgtccgaga aagaattctt aggtggctga cagacgaaga agacagagct   1800

aaagcagtgg gattgcctaa aatcagtttc ctgattgtgg aaatgtcgcc ggtcatcgac   1860

atcgatacaa gcggcataca tgctcttgaa gatctataca agaatcttca gaaaaaagat   1920

atgcagctca ttctgtcgaa tcctggttcc gtcgtcatag aaaaactgca agcgtcgaag   1980

ctcaccgagc acattggaag cagcaatata ttcctcgcgg tctctgacgc tgtgcgattc   2040

tgtacgacga agtcgatgca ggaaccgtga gcgaagtagt tcggaggaat ggctggagtt   2100

gagaatagtt tggccgctcc ctgtgatcta agctgggaca gcgcaatatg atgtggcttt   2160

gtggccaatg tagaaacata taataagtta aggcaatcac cggagcttct ccggtttact   2220

aaaaaaaaaa aaaaaaaaaa aaaaaaaaaa aaaaaaaaaa aaaaaaaaaa aaaaaaaaaa   2280

aaaaaaaaaa aaaaaaaaaa aaaaaaaaaa a                                  2311
```

<210> SEQ ID NO 20
<211> LENGTH: 656
<212> TYPE: PRT
<213> ORGANISM: Triticum aestivum

<400> SEQUENCE: 20

```
Met Val His His Ile Ser Asp Glu Ala Ala Asp Glu Pro Ser Ile Thr
  1               5                  10                  15

Thr Gln Thr Pro Pro Asn Asp Pro Ser Gln Ala Pro Leu Val Tyr Lys
             20                  25                  30

Val Gly Tyr Pro Pro Pro Lys Asn Leu Ala Thr Glu Phe Thr Glu Thr
         35                  40                  45

Leu Arg Glu Thr Phe Phe His Asp Asn Pro Leu Arg Gln Tyr Lys Gly
     50                  55                  60
```

-continued

```
Gln Ser Gly Pro Arg Arg Phe Met Met Gly Leu Glu Phe Leu Phe Pro
 65                  70                  75                  80

Ile Phe Gly Trp Gly Arg Asp Tyr Ser Leu Asn Lys Phe Lys Gly Asp
                 85                  90                  95

Leu Ile Ala Gly Leu Thr Ile Ala Ser Leu Cys Ile Pro Gln Asp Ile
            100                 105                 110

Gly Tyr Ser Lys Leu Ala Asn Leu Asp Pro Gln Tyr Gly Leu Tyr Ser
        115                 120                 125

Ser Phe Ile Pro Pro Leu Ile Tyr Ala Ala Met Gly Ser Ser Arg Asp
    130                 135                 140

Ile Ala Ile Gly Pro Val Ala Val Val Ser Leu Leu Ile Gly Ser Leu
145                 150                 155                 160

Leu Gln Ala Glu Val Asp His Val Lys Asn Lys Glu Glu Tyr Met Arg
                165                 170                 175

Leu Ala Phe Thr Ala Thr Phe Phe Ala Gly Ile Thr Gln Ala Ala Leu
            180                 185                 190

Gly Phe Leu Arg Leu Gly Phe Leu Ile Glu Phe Leu Ser His Ala Ala
        195                 200                 205

Ile Val Gly Phe Met Gly Gly Ala Ala Ile Thr Ile Ala Leu Gln Gln
    210                 215                 220

Leu Lys Tyr Val Leu Gly Ile Ala Asn Phe Thr Arg Lys Thr Asp Ile
225                 230                 235                 240

Val Ser Val Met Glu Ser Val Trp Arg Ser Val His His Gly Trp Asn
                245                 250                 255

Trp Gln Thr Ile Val Ile Gly Val Ser Phe Leu Val Phe Leu Leu Phe
            260                 265                 270

Ala Lys Tyr Ile Gly Lys Lys Lys Arg Lys Leu Phe Trp Val Pro Ala
        275                 280                 285

Ile Ala Pro Ile Ile Ser Val Ile Leu Ala Thr Phe Phe Val Tyr Ile
    290                 295                 300

Thr Arg Ala Asp Lys Gln Gly Val Gln Ile Val Lys His Ile Glu Gln
305                 310                 315                 320

Gly Ile Asn Pro Ser Ser Val His Lys Ile Tyr Phe Thr Gly Pro Phe
                325                 330                 335

Val Ala Lys Gly Phe Lys Ile Gly Val Val Cys Gly Ile Val Gly Leu
            340                 345                 350

Thr Glu Ala Val Ala Ile Gly Arg Thr Phe Ala Ala Met Lys Asp Tyr
        355                 360                 365

Gln Leu Asp Gly Asn Lys Glu Met Val Ala Leu Gly Thr Met Asn Ile
    370                 375                 380

Val Gly Ser Met Thr Ser Cys Tyr Val Thr Thr Gly Ser Phe Ser Arg
385                 390                 395                 400

Ser Ala Val Asn Phe Met Ala Gly Cys Lys Thr Pro Val Ser Asn Val
                405                 410                 415

Val Met Ser Val Val Val Leu Leu Thr Leu Leu Val Ile Thr Pro Leu
            420                 425                 430

Phe Lys Tyr Thr Pro Asn Ala Ile Leu Gly Ser Ile Ile Ile Ser Ala
        435                 440                 445

Val Ile Gly Leu Val Asp Tyr Glu Ala Ala Ile Leu Ile Trp Lys Val
    450                 455                 460

Asp Lys Leu Asp Phe Ile Ala Cys Met Gly Ala Phe Phe Gly Val Val
465                 470                 475                 480
```

-continued

```
Phe Val Ser Val Glu Ile Gly Leu Leu Ile Ala Val Ala Ile Ser Phe
                485                 490                 495

Ala Lys Ile Leu Leu Gln Val Thr Arg Pro Arg Thr Ala Leu Leu Gly
            500                 505                 510

Asn Leu Pro Gly Thr Thr Ile Tyr Arg Asn Ile Ser Gln Tyr Pro Glu
        515                 520                 525

Ala Lys Leu Thr Pro Gly Val Val Ile Val Arg Val Asp Ser Ala Ile
    530                 535                 540

Tyr Phe Ser Asn Ser Asn Tyr Val Arg Glu Arg Ile Leu Arg Trp Leu
545                 550                 555                 560

Thr Asp Glu Glu Asp Arg Ala Lys Ala Val Gly Leu Pro Lys Ile Ser
                565                 570                 575

Phe Leu Ile Val Glu Met Ser Pro Val Ile Asp Ile Asp Thr Ser Gly
            580                 585                 590

Ile His Ala Leu Glu Asp Leu Tyr Lys Asn Leu Gln Lys Lys Asp Met
        595                 600                 605

Gln Leu Ile Leu Ser Asn Pro Gly Ser Val Val Ile Glu Lys Leu Gln
    610                 615                 620

Ala Ser Lys Leu Thr Glu His Ile Gly Ser Ser Asn Ile Phe Leu Ala
625                 630                 635                 640

Val Ser Asp Ala Val Arg Phe Cys Thr Thr Lys Ser Met Gln Glu Pro
                645                 650                 655
```

<210> SEQ ID NO 21
<211> LENGTH: 2022
<212> TYPE: DNA
<213> ORGANISM: Triticum aestivum

<400> SEQUENCE: 21

```
gcacgagggc ggcgatggag agggcgcggg cgatggggcc gtgggagtgg gcggaggcgg      60

ctctcccgtg cttggcgtgg atgcggagct acagatggaa ggaggacttc caggccgacc     120

tcgccgccgg catcactgtc ggcgtcatgc ttgtgcctca ggcaatgtca tatgcaaagc     180

tggctgggct tcacccaatt tatgggctct acacaggctt tgtcccacta tttgtctacg     240

cgatttttgg gtcctcacga caattagcag taggtccagt ggcacttgtc tctctgctag     300

tgtccaatgt tcttgggggt atagttaatt catctagtga gctgtacacg gaattagcca     360

tattattggc attcatggtt ggaatactgg aatgcttgat ggcattgcta agacttggct     420

ggcttattcg tttcattagc cattctgtaa tatctggatt cactacagct tcggccatcg     480

taattggttt gtcccaaatc aagtatttct tgggttacag tgttacaaga agtagcaaaa     540

ttataccact tattgagagt ataattgctg gaatagatca gttctcctgg cctccatttg     600

taatgggatc agcgtttctt gttattcttc taataatgaa aaagctaggg aaaacaaata     660

aaaaattacg tttcctgaga gcttctggtc cactaacagc tgttgttctt ggaacattgt     720

ttgtgaaaat tttccgtcca actgccatat cagtggtagg tgaaataccg caaggccttc     780

ccagtttctc cattcctcga ggatttgaac atctgatgtc cctaatgcca actgcaatac     840

ttatcactgg tgttgctatt ttggagtctg ttgggattgc taaagcgtta gctgcgaaga     900

atggttatga gttggactca aacaaagagt tatttggcct tggcttatca aatatatgcg     960

gttcattctt ctctgcatat cctgctacag gctccttttc taggtctgct gtgaatcatg    1020

aaagcggggc aaagactgga ttatcaggaa tcataatggg cataataatt tgcagtgctc    1080

tcttgtttat gacaccatta tttactgata tacctcagtg tgcattggct gccattgtga    1140
```

-continued

```
tttctgctgt cactggcctg gtagattatg aagaggccat cttcctgtgg ggtattgata   1200

agaaggattt ctttctgtgg gcgatgacat ttactacaac cttaactttt ggcattgaga   1260

ttggtgtcct tgttggggtc gggttttcgc tggcatttgt gatccatgaa tctgcaaatc   1320

cgcatatagc tgttttgggc cgtttgcctg gcaccactgt gtacaggaat acattgcagt   1380

accctgaggc ttatacatac aacgggattg ttgttgtccg tgttgatgca ccaatctact   1440

ttgctaacat aagttacata aaggacaggt tgcgtgagta tgagctcaaa ctcccaaatt   1500

caaaccgtgg acctgatgtt ggaagggtgt actttgtgat cctcgagatg tcccctgtta   1560

catacatcga ctcgagcgct gttcaagctc tcaaggacct gcaccaagaa tacaaagcac   1620

gcgacatcca gattgctata gcgaatccta accggcaggt gcacctattg ctgtcaagag   1680

cgggcatcat cgacatgatt ggcgcagggt ggtgtttcgt ccgagtgcac gacgcggtgc   1740

aagtatgcct ccagcatgtg cggagttcat cgtcgaatgc cattaagtta tccccacagg   1800

cgtctgggaa cttgacggag tctcccaagg cgcagcagcg gtatggcttc ctgaggaacc   1860

tctggaaagc acaagacggt aatgggagcg ccggtgacga ggcccaatcg ttgctgcgcc   1920

aaaaccttgt gtagccaatt gtctccctcc ctcagtgcaa tcatgatgca tgcatttgta   1980

tttgtgttgt tgtatgcatg tagattgtgc aggaaaaaaa aa                      2022
```

```
<210> SEQ ID NO 22
<211> LENGTH: 593
<212> TYPE: PRT
<213> ORGANISM: Triticum aestivum

<400> SEQUENCE: 22

Thr Arg Ala Ala Met Glu Arg Ala Arg Ala Met Gly Pro Trp Glu Trp
  1               5                  10                  15

Ala Glu Ala Ala Leu Pro Cys Leu Ala Trp Met Arg Ser Tyr Arg Trp
             20                  25                  30

Lys Glu Asp Phe Gln Ala Asp Leu Ala Ala Gly Ile Thr Val Gly Val
         35                  40                  45

Met Leu Val Pro Gln Ala Met Ser Tyr Ala Lys Leu Ala Gly Leu His
     50                  55                  60

Pro Ile Tyr Gly Leu Tyr Thr Gly Phe Val Pro Leu Phe Val Tyr Ala
 65                  70                  75                  80

Ile Phe Gly Ser Ser Arg Gln Leu Ala Val Gly Pro Val Ala Leu Val
                 85                  90                  95

Ser Leu Leu Val Ser Asn Val Leu Gly Gly Ile Val Asn Ser Ser Ser
            100                 105                 110

Glu Leu Tyr Thr Glu Leu Ala Ile Leu Leu Ala Phe Met Val Gly Ile
        115                 120                 125

Leu Glu Cys Leu Met Ala Leu Leu Arg Leu Gly Trp Leu Ile Arg Phe
    130                 135                 140

Ile Ser His Ser Val Ile Ser Gly Phe Thr Thr Ala Ser Ala Ile Val
145                 150                 155                 160

Ile Gly Leu Ser Gln Ile Lys Tyr Phe Leu Gly Tyr Ser Val Thr Arg
                165                 170                 175

Ser Ser Lys Ile Ile Pro Leu Ile Glu Ser Ile Ile Ala Gly Ile Asp
            180                 185                 190

Gln Phe Ser Trp Pro Pro Phe Val Met Gly Ser Ala Phe Leu Val Ile
        195                 200                 205

Leu Leu Ile Met Lys Lys Leu Gly Lys Thr Asn Lys Lys Leu Arg Phe
    210                 215                 220
```

-continued

```
Leu Arg Ala Ser Gly Pro Leu Thr Ala Val Val Leu Gly Thr Leu Phe
225                 230                 235                 240

Val Lys Ile Phe Arg Pro Thr Ala Ile Ser Val Val Gly Glu Ile Pro
                245                 250                 255

Gln Gly Leu Pro Ser Phe Ser Ile Pro Arg Gly Phe Glu His Leu Met
            260                 265                 270

Ser Leu Met Pro Thr Ala Ile Leu Ile Thr Gly Val Ala Ile Leu Glu
        275                 280                 285

Ser Val Gly Ile Ala Lys Ala Leu Ala Ala Lys Asn Gly Tyr Glu Leu
    290                 295                 300

Asp Ser Asn Lys Glu Leu Phe Gly Leu Gly Leu Ser Asn Ile Cys Gly
305                 310                 315                 320

Ser Phe Phe Ser Ala Tyr Pro Ala Thr Gly Ser Phe Ser Arg Ser Ala
                325                 330                 335

Val Asn His Glu Ser Gly Ala Lys Thr Gly Leu Ser Gly Ile Ile Met
            340                 345                 350

Gly Ile Ile Ile Cys Ser Ala Leu Leu Phe Met Thr Pro Leu Phe Thr
        355                 360                 365

Asp Ile Pro Gln Cys Ala Leu Ala Ala Ile Val Ile Ser Ala Val Thr
    370                 375                 380

Gly Leu Val Asp Tyr Glu Glu Ala Ile Phe Leu Trp Gly Ile Asp Lys
385                 390                 395                 400

Lys Asp Phe Phe Leu Trp Ala Met Thr Phe Thr Thr Thr Leu Thr Phe
                405                 410                 415

Gly Ile Glu Ile Gly Val Leu Val Gly Val Gly Phe Ser Leu Ala Phe
            420                 425                 430

Val Ile His Glu Ser Ala Asn Pro His Ile Ala Val Leu Gly Arg Leu
        435                 440                 445

Pro Gly Thr Thr Val Tyr Arg Asn Thr Leu Gln Tyr Pro Glu Ala Tyr
    450                 455                 460

Thr Tyr Asn Gly Ile Val Val Val Arg Val Asp Ala Pro Ile Tyr Phe
465                 470                 475                 480

Ala Asn Ile Ser Tyr Ile Lys Asp Arg Leu Arg Glu Tyr Glu Leu Lys
                485                 490                 495

Leu Pro Asn Ser Asn Arg Gly Pro Asp Val Gly Arg Val Tyr Phe Val
            500                 505                 510

Ile Leu Glu Met Ser Pro Val Thr Tyr Ile Asp Ser Ser Ala Val Gln
        515                 520                 525

Ala Leu Lys Asp Leu His Gln Glu Tyr Lys Ala Arg Asp Ile Gln Ile
    530                 535                 540

Ala Ile Ala Asn Pro Asn Arg Gln Val His Leu Leu Leu Ser Arg Ala
545                 550                 555                 560

Gly Ile Ile Asp Met Ile Gly Ala Gly Trp Cys Phe Val Arg Val His
                565                 570                 575

Asp Ala Val Gln Val Cys Leu Gln His Val Arg Ser Ser Ser Ser Asn
            580                 585                 590

Ala
```

<210> SEQ ID NO 23
<211> LENGTH: 660
<212> TYPE: PRT
<213> ORGANISM: Sporobolus stapfianus

<400> SEQUENCE: 23

-continued

```
Met Val Gly Met Arg Val Pro Tyr Gly Gly Ser Tyr Thr Asn Asn Gly
  1               5                  10                  15

Ser Asn Glu Ser Gln Pro Pro Gly Ala Ala Pro Glu Val Pro Ala Met
            20                  25                  30

Val Glu Val His Lys Val Val Pro Pro Pro Pro Gln Ser Thr Ala Ser
        35                  40                  45

Lys Leu Lys Thr Arg Leu Lys Glu Thr Leu Phe Pro Asp Asp Pro Phe
    50                  55                  60

Arg Gly Phe Gln Gly Gln Pro Ala Arg Val Gln Trp Val Leu Ala Val
 65                  70                  75                  80

Lys Tyr Leu Phe Pro Ile Leu Asp Trp Leu Pro Ala Tyr Ser Leu Ser
                 85                  90                  95

Leu Phe Lys Ser Asp Leu Ile Ala Gly Leu Thr Ile Ala Ser Leu Ala
            100                 105                 110

Ile Pro Gln Gly Ile Ser Tyr Ala Lys Leu Ala Asn Leu Pro Pro Leu
        115                 120                 125

Ile Gly Leu Tyr Ser Ser Phe Val Pro Pro Leu Val Tyr Ala Val Leu
    130                 135                 140

Gly Ser Ser Arg Asp Leu Ala Val Gly Pro Val Ser Ile Ser Ser Leu
145                 150                 155                 160

Ile Met Gly Pro Cys Cys Ala Ser Arg Gln Pro His Cys Gly Ala Asp
                165                 170                 175

Ala Val Pro Ala Ala Arg Leu His Ala Thr Leu Phe Ala Gly Ile Phe
            180                 185                 190

Gln Ala Ser Leu Gly Ile Leu Arg Leu Gly Phe Ile Ile Asp Phe Leu
        195                 200                 205

Ser Lys Ala Thr Leu Val Gly Phe Met Ala Gly Ala Ala Ile Ile Val
    210                 215                 220

Ser Leu Gln Gln Leu Lys Ala Leu Leu Gly Ile Val His Phe Thr Thr
225                 230                 235                 240

Glu Met Gly Ile Val Pro Val Met Ala Ser Val Phe His His Thr Lys
                245                 250                 255

Glu Trp Ser Trp Gln Thr Ile Leu Met Gly Val Cys Phe Leu Val Phe
            260                 265                 270

Leu Leu Val Ala Arg His Val Ser Ile Arg Trp Pro Arg Leu Phe Trp
        275                 280                 285

Val Ser Ala Cys Ala Pro Leu Val Ser Val Ile Ile Ser Thr Leu Val
    290                 295                 300

Val Phe Leu Phe Lys Ala Gln Asn His Gly Ile Ser Ile Ile Gly Gln
305                 310                 315                 320

Leu Lys Cys Gly Leu Asn Arg Pro Ser Trp Asp Lys Thr Asn Ile Asp
                325                 330                 335

Thr Thr Tyr Leu Gly Leu Thr Met Lys Thr Gly Leu Val Thr Gly Ile
            340                 345                 350

Ile Ser Leu Thr Glu Gly Ile Ala Val Gly Arg Thr Phe Ala Ser Leu
        355                 360                 365

Lys Glu Tyr Gln Ile Asp Gly Asn Lys Glu Met Met Ala Ile Gly Leu
    370                 375                 380

Met Asn Val Val Gly Ser Cys Thr Ser Cys Tyr Val Thr Thr Gly Ala
385                 390                 395                 400

Phe Ser Arg Ser Pro Val Asn His Asn Ala Gly Cys Lys Thr Ala Met
                405                 410                 415
```

-continued

```
Ser Asn Val Ile Met Ala Leu Thr Val Met Val Thr Leu Leu Phe Leu
            420                 425                 430

Met Pro Leu Phe Val Tyr Thr Pro Asn Val Val Leu Gly Ala Ile Ile
        435                 440                 445

Ile Ala Ala Val Ile Gly Leu Ile Asp Ile Pro Ala Val Tyr His Ile
    450                 455                 460

Trp Lys Met Asp Lys Met Asp Phe Leu Val Cys Val Cys Ala Phe Ala
465                 470                 475                 480

Gly Val Leu Phe Ile Ser Val Gln Glu Gly Leu Ala Ile Ala Val Gly
                485                 490                 495

Ile Ser Val Phe Arg Val Leu Leu Gln Ile Thr Arg Pro Lys Ile Thr
            500                 505                 510

Val Gln Gly Asn Ile Met Gly Thr Asp Ile Tyr Arg Asn Leu His Gln
        515                 520                 525

Tyr Lys Asp Ala Gln Arg Ile Pro Gly Phe Leu Ile Leu Ala Thr Glu
    530                 535                 540

Ala Pro Ile Asn Phe Ala Asn Ser Asn Tyr Leu Asn Glu Arg Ile Lys
545                 550                 555                 560

Arg Trp Ile Glu Glu Glu Ser Ser Ala Gln Thr Lys Gln Thr Glu Leu
                565                 570                 575

Arg Phe Val Ile Leu Asp Leu Ser Ala Val Pro Ala Ile Asp Thr Ser
            580                 585                 590

Gly Val Ala Phe Leu Ile Asp Ile Lys Lys Ser Ile Glu Lys Arg Gly
        595                 600                 605

Leu Glu Leu Val Leu Val Asn Pro Thr Gly Glu Gly His Gly Lys Asn
    610                 615                 620

Thr Ala Ser Glu Arg Gly Thr Gln Ala Phe Gln Val Gly Ile Ala Cys
625                 630                 635                 640

Ile Leu Thr Thr Gly Glu Ala Val Ala Ser Leu Ser Ala Leu Ala Lys
                645                 650                 655

Met Ala Ser Pro
            660


<210> SEQ ID NO 24
<211> LENGTH: 658
<212> TYPE: PRT
<213> ORGANISM: Arabidopsis thaliana

<400> SEQUENCE: 24

Met Gly Thr Glu Asp Tyr Thr Phe Pro Gln Gly Ala Glu Glu Leu His
  1               5                  10                  15

Arg Arg His His Thr Val Glu Ala Pro Gln Pro Gln Pro Phe Leu Lys
             20                  25                  30

Ser Leu Gln Tyr Ser Val Lys Glu Thr Leu Phe Pro Asp Asp Pro Phe
         35                  40                  45

Arg Gln Phe Lys Asn Gln Asn Ala Ser Arg Lys Phe Val Leu Gly Leu
     50                  55                  60

Lys Tyr Phe Leu Pro Ile Phe Glu Trp Ala Pro Arg Tyr Asn Leu Lys
 65                  70                  75                  80

Phe Phe Lys Ser Asp Leu Ile Ala Gly Ile Thr Ile Ala Ser Leu Ala
                 85                  90                  95

Ile Pro Gln Gly Ile Ser Tyr Ala Lys Leu Ala Asn Leu Pro Pro Ile
            100                 105                 110

Leu Gly Leu Tyr Ser Ser Phe Val Pro Pro Leu Val Tyr Ala Val Leu
        115                 120                 125
```

-continued

```
Gly Ser Ser Arg Asp Leu Ala Val Gly Thr Val Ala Val Ala Ser Leu
    130                 135                 140

Leu Thr Gly Ala Met Leu Ser Lys Glu Val Asp Ala Glu Lys Asp Pro
145                 150                 155                 160

Lys Leu Tyr Leu His Leu Ala Phe Thr Ala Thr Phe Phe Ala Gly Val
                165                 170                 175

Leu Glu Ala Ser Leu Gly Ile Phe Arg Leu Gly Phe Ile Val Asp Phe
            180                 185                 190

Leu Ser His Ala Thr Ile Val Gly Phe Met Gly Gly Ala Ala Thr Val
        195                 200                 205

Val Ser Leu Gln Gln Leu Lys Gly Ile Phe Gly Leu Lys His Phe Thr
    210                 215                 220

Asp Ser Thr Asp Val Ile Ser Val Met Arg Ser Val Phe Ser Gln Thr
225                 230                 235                 240

His Glu Trp Arg Trp Glu Ser Gly Val Leu Gly Cys Gly Phe Leu Phe
                245                 250                 255

Phe Leu Leu Ser Thr Arg Tyr Phe Ser Ile Lys Lys Pro Lys Phe Phe
            260                 265                 270

Trp Val Ala Ala Met Ala Pro Leu Thr Ser Val Ile Leu Gly Ser Leu
        275                 280                 285

Leu Val Tyr Phe Thr His Ala Glu Arg His Gly Val Gln Val Ile Gly
    290                 295                 300

Asp Leu Lys Lys Gly Leu Asn Pro Leu Ser Gly Ser Asp Leu Ile Phe
305                 310                 315                 320

Thr Ser Pro Tyr Met Ser Thr Ala Val Lys Thr Gly Leu Ile Thr Gly
                325                 330                 335

Ile Ile Ala Leu Ala Glu Gly Ile Ala Val Gly Arg Ser Phe Ala Met
            340                 345                 350

Phe Lys Asn Tyr Asn Ile Asp Gly Asn Lys Glu Met Ile Ala Phe Gly
        355                 360                 365

Met Met Asn Ile Val Gly Ser Phe Thr Ser Cys Tyr Leu Thr Thr Gly
    370                 375                 380

Pro Phe Ser Arg Ser Ala Val Asn Tyr Asn Ala Gly Cys Lys Thr Ala
385                 390                 395                 400

Met Ser Asn Ile Val Met Ala Ile Ala Val Met Phe Thr Leu Leu Phe
                405                 410                 415

Leu Thr Pro Leu Phe His Tyr Thr Pro Leu Val Val Leu Ser Ala Ile
            420                 425                 430

Ile Ile Ser Ala Met Leu Gly Leu Ile Asp Tyr Gln Ala Ala Ile His
        435                 440                 445

Leu Trp Lys Val Asp Lys Phe Asp Phe Leu Val Cys Met Ser Ala Tyr
    450                 455                 460

Val Gly Val Val Phe Gly Ser Val Glu Ile Gly Leu Val Val Ala Val
465                 470                 475                 480

Ala Ile Ser Ile Ala Arg Leu Leu Leu Phe Val Ser Arg Pro Lys Thr
                485                 490                 495

Ala Val Lys Gly Asn Ile Pro Asn Ser Met Ile Tyr Arg Asn Thr Glu
            500                 505                 510

Gln Tyr Pro Ser Ser Arg Thr Val Pro Gly Ile Leu Ile Leu Glu Ile
        515                 520                 525

Asp Ala Pro Ile Tyr Phe Ala Asn Ala Ser Tyr Leu Arg Glu Arg Ile
    530                 535                 540
```

-continued

```
Ile Arg Trp Ile Asp Glu Glu Glu Glu Arg Val Lys Gln Ser Gly Glu
545                 550                 555                 560

Ser Ser Leu Gln Tyr Ile Ile Leu Asp Met Ser Ala Val Gly Asn Ile
                565                 570                 575

Asp Thr Ser Gly Ile Ser Met Met Val Glu Ile Lys Lys Val Ile Asp
            580                 585                 590

Arg Arg Ala Leu Lys Leu Val Leu Ser Asn Pro Lys Gly Glu Val Val
        595                 600                 605

Lys Lys Leu Thr Arg Ser Lys Phe Ile Gly Asp His Leu Gly Lys Glu
    610                 615                 620

Trp Met Phe Leu Thr Val Gly Glu Ala Val Glu Ala Cys Ser Tyr Met
625                 630                 635                 640

Leu His Thr Phe Lys Thr Glu Pro Ala Ser Lys Asn Glu Pro Trp Asn
                645                 650                 655

Asn Val


<210> SEQ ID NO 25
<211> LENGTH: 644
<212> TYPE: PRT
<213> ORGANISM: Stylosanthes hamata

<400> SEQUENCE: 25

Met Ser Ser Leu Gly Thr Glu Gln Phe Ser Glu Arg Ser Gln Trp Val
  1               5                  10                  15

Leu Asn Ser Pro Asn Pro Pro Pro Leu Thr Lys Lys Phe Leu Gly Pro
             20                  25                  30

Leu Lys Asp Asn Lys Phe Phe Thr Ser Ser Ser Ser Lys Lys Glu Thr
         35                  40                  45

Arg Ala Val Ser Phe Leu Ala Ser Leu Phe Pro Ile Leu Ser Trp Ile
     50                  55                  60

Arg Thr Tyr Ser Ala Thr Lys Phe Lys Asp Asp Leu Leu Ser Gly Leu
 65                  70                  75                  80

Thr Leu Ala Ser Leu Ser Ile Pro Gln Ser Ile Gly Tyr Ala Asn Leu
                 85                  90                  95

Ala Lys Leu Asp Pro Gln Tyr Gly Leu Tyr Thr Ser Val Ile Pro Pro
            100                 105                 110

Val Ile Tyr Ala Leu Met Gly Ser Ser Arg Glu Ile Ala Ile Gly Pro
        115                 120                 125

Val Ala Val Val Ser Met Leu Leu Ser Ser Leu Val Pro Lys Val Ile
    130                 135                 140

Asp Pro Asp Ala His Pro Asn Asp Tyr Arg Asn Leu Val Phe Thr Val
145                 150                 155                 160

Thr Leu Phe Ala Gly Ile Phe Gln Thr Ala Phe Gly Val Leu Arg Leu
                165                 170                 175

Gly Phe Leu Val Asp Phe Leu Ser His Ala Ala Leu Val Gly Phe Met
            180                 185                 190

Ala Gly Ala Ala Ile Val Ile Gly Leu Gln Gln Leu Lys Gly Leu Leu
        195                 200                 205

Gly Leu Thr His Phe Thr Thr Lys Thr Asp Ala Val Ala Val Leu Lys
    210                 215                 220

Ser Val Tyr Thr Ser Leu His Gln Gln Ile Thr Ser Ser Glu Asn Trp
225                 230                 235                 240

Ser Pro Leu Asn Phe Val Ile Gly Cys Ser Phe Leu Ile Phe Leu Leu
                245                 250                 255
```

-continued

```
Ala Ala Arg Phe Ile Gly Arg Arg Asn Lys Lys Phe Phe Trp Leu Pro
            260                 265                 270

Ala Ile Ala Pro Leu Leu Ser Val Ile Leu Ser Thr Leu Ile Val Phe
        275                 280                 285

Leu Ser Lys Gly Asp Lys His Gly Val Asn Ile Ile Lys His Val Gln
    290                 295                 300

Gly Gly Leu Asn Pro Ser Ser Val His Lys Leu Gln Leu Asn Gly Pro
305                 310                 315                 320

His Val Gly Gln Ala Ala Lys Ile Gly Leu Ile Ser Ala Ile Ile Ala
                325                 330                 335

Leu Thr Glu Ala Ile Ala Val Gly Arg Ser Phe Ala Asn Ile Lys Gly
            340                 345                 350

Tyr His Leu Asp Gly Asn Lys Glu Met Leu Ala Met Gly Cys Met Asn
        355                 360                 365

Ile Ala Gly Ser Leu Thr Ser Cys Tyr Val Ser Thr Gly Ser Phe Ser
    370                 375                 380

Arg Thr Ala Val Asn Phe Ser Ala Gly Cys Lys Thr Ala Val Ser Asn
385                 390                 395                 400

Ile Val Met Ala Val Thr Val Leu Leu Cys Leu Glu Leu Phe Thr Arg
                405                 410                 415

Leu Leu Tyr Tyr Thr Pro Met Ala Ile Leu Ala Ser Ile Ile Leu Ser
            420                 425                 430

Ala Leu Pro Gly Leu Ile Asp Ile Gly Glu Ala Tyr His Ile Trp Lys
        435                 440                 445

Val Asp Lys Phe Asp Phe Leu Ala Cys Leu Gly Ala Phe Phe Gly Val
    450                 455                 460

Leu Phe Val Ser Ile Glu Ile Gly Leu Leu Ile Ala Leu Ser Ile Ser
465                 470                 475                 480

Phe Ala Lys Ile Leu Leu Gln Ala Ile Arg Pro Gly Val Glu Val Leu
                485                 490                 495

Gly Arg Ile Pro Thr Thr Glu Ala Tyr Cys Asp Val Ala Gln Tyr Pro
            500                 505                 510

Met Ala Val Thr Thr Pro Gly Ile Leu Val Ile Arg Ile Ser Ser Gly
        515                 520                 525

Ser Leu Cys Phe Ala Asn Ala Gly Phe Val Arg Glu Arg Ile Leu Lys
    530                 535                 540

Trp Val Glu Asp Glu Glu Gln Asp Asn Ile Glu Glu Ala Ala Lys Gly
545                 550                 555                 560

Arg Val Gln Ala Ile Ile Ile Asp Met Thr Asp Leu Thr Asn Val Asp
                565                 570                 575

Thr Ser Gly Ile Leu Ala Leu Glu Glu Leu His Lys Lys Leu Leu Ser
            580                 585                 590

Arg Gly Val Glu Leu Ala Met Val Asn Pro Arg Trp Glu Val Ile His
        595                 600                 605

Lys Leu Lys Val Ala Asn Phe Val Asp Lys Ile Gly Lys Glu Arg Val
    610                 615                 620

Phe Leu Thr Val Ala Glu Ala Val Asp Ala Cys Leu Ser Ser Arg Phe
625                 630                 635                 640

Ala Asn Ser Ala
```

<210> SEQ ID NO 26
<211> LENGTH: 646
<212> TYPE: PRT
<213> ORGANISM: Arabidopsis thaliana -continued

<400> SEQUENCE: 26

```
Met Gly Thr Glu Asp Tyr Thr Phe Pro Gln Gly Ala Glu Glu Leu His
  1               5                  10                  15

Arg Arg His His Thr Val Glu Ala Pro Gln Pro Gln Pro Phe Leu Lys
             20                  25                  30

Ser Leu Gln Tyr Ser Val Lys Glu Thr Leu Phe Pro Asp Asp Pro Phe
         35                  40                  45

Arg Gln Phe Lys Asn Gln Asn Ala Ser Arg Lys Phe Val Leu Gly Leu
     50                  55                  60

Lys Tyr Phe Leu Pro Ile Phe Glu Trp Ala Pro Arg Tyr Asn Leu Lys
 65                  70                  75                  80

Phe Phe Lys Ser Asp Leu Ile Ala Gly Ile Thr Ile Ala Ser Leu Ala
                 85                  90                  95

Ile Pro Gln Gly Ile Ser Tyr Ala Lys Leu Ala Asn Leu Pro Pro Ile
            100                 105                 110

Leu Gly Leu Tyr Ser Ser Phe Val Pro Pro Leu Val Tyr Ala Val Leu
        115                 120                 125

Gly Ser Ser Arg Asp Leu Ala Val Gly Thr Val Ala Val Ala Ser Leu
    130                 135                 140

Leu Thr Gly Ala Met Leu Ser Lys Glu Val Asp Ala Glu Lys Asp Pro
145                 150                 155                 160

Lys Leu Tyr Leu His Leu Ala Phe Thr Ala Thr Phe Phe Ala Gly Val
                165                 170                 175

Leu Glu Ala Ser Leu Gly Ile Phe Arg Leu Gly Phe Ile Val Asp Phe
            180                 185                 190

Leu Ser His Ala Thr Ile Val Gly Phe Met Gly Gly Ala Ala Thr Val
        195                 200                 205

Val Ser Leu Gln Gln Leu Lys Gly Ile Phe Gly Leu Lys His Phe Thr
    210                 215                 220

Asp Ser Thr Asp Val Ile Ser Val Met Arg Ser Val Phe Ser Gln Thr
225                 230                 235                 240

His Glu Trp Arg Trp Glu Ser Gly Val Leu Gly Cys Gly Phe Leu Phe
                245                 250                 255

Phe Leu Leu Ser Thr Arg Tyr Phe Ser Ile Lys Lys Pro Lys Phe Phe
            260                 265                 270

Trp Val Ala Ala Met Ala Pro Leu Thr Ser Val Ile Leu Gly Ser Leu
        275                 280                 285

Leu Val Tyr Phe Thr His Ala Glu Arg His Gly Val Gln Val Gly Ser
    290                 295                 300

Asp Leu Ile Phe Thr Ser Pro Tyr Met Ser Thr Ala Val Lys Thr Gly
305                 310                 315                 320

Leu Ile Thr Gly Ile Ile Ala Leu Ala Glu Gly Val Ala Val Gly Arg
                325                 330                 335

Ser Phe Ala Met Phe Lys Asn Tyr Asn Ile Asp Gly Asn Lys Glu Met
            340                 345                 350

Ile Ala Phe Gly Met Met Asn Ile Val Gly Ser Phe Thr Ser Cys Tyr
        355                 360                 365

Leu Thr Thr Gly Pro Phe Ser Arg Ser Ala Val Asn Tyr Asn Ala Gly
    370                 375                 380

Cys Lys Thr Ala Met Ser Asn Ile Val Met Ala Ile Ala Val Met Phe
385                 390                 395                 400

Thr Leu Leu Phe Leu Thr Pro Leu Phe His Tyr Thr Pro Leu Val Val
```

-continued

```
                405                 410                 415

Leu Ser Ala Ile Ile Ile Ser Ala Met Leu Gly Leu Ile Asp Tyr Gln
            420                 425                 430

Ala Ala Ile His Leu Trp Lys Val Asp Lys Phe Asp Phe Leu Val Cys
        435                 440                 445

Met Ser Ala Tyr Val Gly Val Val Phe Gly Ser Val Glu Ile Gly Leu
    450                 455                 460

Val Val Ala Val Ala Ile Ser Ile Ala Arg Leu Leu Leu Phe Val Ser
465                 470                 475                 480

Arg Pro Lys Thr Ala Val Lys Gly Asn Ile Pro Asn Ser Met Ile Tyr
                485                 490                 495

Arg Asn Thr Glu Gln Tyr Pro Ser Ser Arg Thr Val Pro Gly Ile Leu
            500                 505                 510

Ile Leu Glu Ile Asp Ala Pro Ile Tyr Phe Ala Asn Ala Ser Tyr Leu
        515                 520                 525

Arg Glu Arg Ile Ile Arg Trp Ile Asp Glu Glu Glu Glu Arg Val Lys
    530                 535                 540

Gln Ser Gly Glu Ser Ser Leu Gln Tyr Ile Ile Leu Asp Met Ser Ala
545                 550                 555                 560

Val Gly Asn Ile Asp Thr Ser Gly Ile Ser Met Met Val Glu Ile Lys
                565                 570                 575

Lys Val Ile Asp Arg Arg Ala Leu Lys Leu Val Leu Ser Asn Pro Lys
            580                 585                 590

Gly Glu Val Val Lys Lys Leu Thr Arg Ser Lys Phe Ile Gly Asp His
        595                 600                 605

Leu Gly Lys Glu Trp Met Phe Leu Thr Val Gly Glu Ala Val Glu Ala
    610                 615                 620

Cys Ser Tyr Met Leu His Thr Phe Lys Thr Glu Pro Ala Ser Lys Asn
625                 630                 635                 640

Glu Pro Trp Asn Asn Val
                645


<210> SEQ ID NO 27
<211> LENGTH: 233
<212> TYPE: PRT
<213> ORGANISM: Zea mays

<400> SEQUENCE: 27

Ala Ile Gly Pro Val Ala Val Val Ser Leu Leu Leu Gly Thr Leu Leu
  1               5                  10                  15

Gln Asn Glu Ile Asp Pro Lys Thr His Pro Leu Glu Tyr Arg Arg Leu
            20                  25                  30

Ala Phe Thr Ala Thr Phe Phe Ala Gly Val Thr Gln Ala Ala Leu Gly
        35                  40                  45

Phe Phe Arg Leu Gly Phe Ile Ile Glu Phe Leu Ser His Ala Ala Ile
     50                  55                  60

Val Gly Phe Met Ala Gly Ala Ala Ile Thr Ile Ala Leu Gln Gln Leu
 65                  70                  75                  80

Lys Gly Phe Leu Gly Ile Ala Asn Phe Thr Lys Lys Ser Asp Ile Val
                 85                  90                  95

Ser Val Met Lys Ser Val Trp Gly Asn Val His His Gly Trp Asn Trp
            100                 105                 110

Gln Thr Ile Leu Ile Gly Ala Thr Phe Leu Ala Phe Leu Leu Val Ala
        115                 120                 125
```

-continued

```
Lys Tyr Ile Gly Lys Arg Asn Lys Lys Leu Phe Trp Val Ser Ala Ile
    130                 135                 140

Ala Pro Leu Thr Ser Val Ile Ile Ser Thr Phe Phe Val Tyr Ile Thr
145                 150                 155                 160

Arg Ala Asp Lys His Gly Val Ala Ile Val Lys Asn Ile Arg Lys Gly
                165                 170                 175

Ile Asn Pro Pro Ser Ala Ser Leu Ile Tyr Phe Thr Gly Pro Tyr Leu
            180                 185                 190

Ala Thr Gly Phe Lys Ile Gly Ile Val Ala Gly Met Ile Gly Leu Thr
        195                 200                 205

Glu Ala Ile Ala Ile Gly Arg Thr Phe Ala Ala Leu Lys Asp Tyr Arg
    210                 215                 220

Ile Asp Gly Asn Lys Glu Met Val Ala
225                 230


<210> SEQ ID NO 28
<211> LENGTH: 646
<212> TYPE: PRT
<213> ORGANISM: Arabidopsis thaliana

<400> SEQUENCE: 28

Met Ser Ser Lys Arg Ala Ser Gln Tyr His Gln Val Glu Ile Pro Pro
  1               5                  10                  15

Pro Gln Pro Phe Leu Lys Ser Leu Lys Asn Thr Leu Asn Glu Ile Leu
             20                  25                  30

Phe Ala Asp Asp Pro Phe Arg Arg Ile Arg Asn Glu Ser Lys Thr Ser
         35                  40                  45

Lys Lys Ile Glu Leu Gly Leu Arg His Val Phe Pro Ile Leu Glu Trp
     50                  55                  60

Ala Arg Gly Tyr Ser Leu Glu Tyr Leu Lys Ser Asp Val Ile Ser Gly
 65                  70                  75                  80

Ile Thr Ile Ala Ser Leu Ala Ile Pro Gln Gly Ile Ser Tyr Ala Gln
                 85                  90                  95

Leu Ala Asn Leu Pro Pro Ile Leu Gly Leu Tyr Ser Ser Leu Val Pro
            100                 105                 110

Pro Leu Val Tyr Ala Ile Met Gly Ser Ser Arg Asp Leu Ala Val Gly
        115                 120                 125

Thr Val Ala Val Ala Ser Leu Leu Thr Ala Ala Met Leu Gly Lys Glu
    130                 135                 140

Val Asn Ala Val Val Asn Pro Lys Leu Tyr Leu His Leu Ala Phe Thr
145                 150                 155                 160

Ala Thr Phe Phe Ala Gly Leu Met Gln Thr Cys Leu Gly Leu Leu Arg
                165                 170                 175

Leu Gly Phe Val Val Glu Ile Leu Ser His Ala Ala Ile Val Gly Phe
            180                 185                 190

Met Gly Gly Ala Ala Thr Val Val Cys Leu Gln Gln Leu Lys Gly Leu
        195                 200                 205

Leu Gly Leu His His Phe Thr His Ser Thr Asp Ile Val Thr Val Leu
    210                 215                 220

Arg Ser Ile Phe Ser Gln Ser His Met Trp Arg Trp Glu Ser Gly Val
225                 230                 235                 240

Leu Gly Cys Cys Phe Leu Ile Phe Leu Leu Thr Thr Lys Tyr Ile Ser
                245                 250                 255

Lys Lys Arg Pro Lys Leu Phe Trp Ile Ser Ala Met Ser Pro Leu Val
            260                 265                 270
```

-continued

```
Ser Val Ile Phe Gly Thr Ile Phe Leu Tyr Phe Leu His Asp Gln Phe
        275                 280                 285

His Gly Ile Gln Phe Ile Gly Glu Leu Lys Lys Gly Ile Asn Pro Pro
    290                 295                 300

Ser Ile Thr His Leu Val Phe Thr Pro Pro Tyr Val Met Leu Ala Leu
305                 310                 315                 320

Lys Val Gly Ile Ile Thr Gly Val Ile Ala Leu Ala Glu Gly Ile Ala
                325                 330                 335

Val Gly Arg Ser Phe Ala Met Tyr Lys Asn Tyr Asn Ile Asp Gly Asn
            340                 345                 350

Lys Glu Met Ile Ala Phe Gly Met Met Asn Ile Leu Gly Ser Phe Ser
        355                 360                 365

Ser Cys Tyr Leu Thr Thr Gly Pro Phe Ser Arg Ser Ala Val Asn Tyr
    370                 375                 380

Asn Ala Gly Cys Lys Thr Ala Leu Ser Asn Val Val Met Ala Val Ala
385                 390                 395                 400

Val Ala Val Thr Leu Leu Phe Leu Thr Pro Leu Phe Phe Tyr Thr Pro
                405                 410                 415

Leu Val Val Leu Ser Ser Ile Ile Ile Ala Ala Met Leu Gly Leu Val
            420                 425                 430

Asp Tyr Glu Ala Ala Ile His Leu Trp Lys Leu Asp Lys Phe Asp Phe
        435                 440                 445

Phe Val Cys Leu Ser Ala Tyr Leu Gly Val Val Phe Gly Thr Ile Glu
    450                 455                 460

Ile Gly Leu Ile Leu Ser Val Gly Ile Ser Val Met Arg Leu Val Leu
465                 470                 475                 480

Phe Val Gly Arg Pro Lys Ile Tyr Val Met Gly Asn Ile Gln Asn Ser
                485                 490                 495

Glu Ile Tyr Arg Asn Ile Glu His Tyr Pro Gln Ala Ile Thr Arg Ser
            500                 505                 510

Ser Leu Leu Ile Leu His Ile Asp Gly Pro Ile Tyr Phe Ala Asn Ser
        515                 520                 525

Thr Tyr Leu Arg Asp Arg Ile Gly Arg Trp Ile Asp Glu Glu Glu Asp
    530                 535                 540

Lys Leu Arg Thr Ser Gly Asp Ile Ser Leu Gln Tyr Ile Val Leu Asp
545                 550                 555                 560

Met Ser Ala Val Gly Asn Ile Asp Thr Ser Gly Ile Ser Met Leu Glu
                565                 570                 575

Glu Leu Asn Lys Ile Leu Gly Arg Arg Glu Leu Lys Leu Val Ile Ala
            580                 585                 590

Asn Pro Gly Ala Glu Val Met Lys Lys Leu Ser Lys Ser Thr Phe Ile
        595                 600                 605

Glu Ser Ile Gly Lys Glu Arg Ile Tyr Leu Thr Val Ala Glu Ala Val
    610                 615                 620

Ala Ala Cys Asp Phe Met Leu His Thr Ala Lys Pro Asp Ser Pro Val
625                 630                 635                 640

Pro Glu Phe Asn Asn Val
                645
```

<210> SEQ ID NO 29
<211> LENGTH: 631
<212> TYPE: PRT
<213> ORGANISM: Arabidopsis thaliana -continued

<400> SEQUENCE: 29

```
Met Glu Val His Lys Val Val Ala Pro Pro His Lys Ser Thr Val Ala
  1               5                  10                  15

Lys Leu Lys Thr Lys Leu Lys Glu Thr Phe Phe Pro Asp Asp Pro Leu
             20                  25                  30

Arg Gln Phe Arg Gly Gln Pro Asn Arg Thr Lys Leu Ile Arg Ala Ala
         35                  40                  45

Gln Tyr Ile Phe Pro Ile Leu Gln Trp Cys Pro Glu Tyr Ser Phe Ser
     50                  55                  60

Leu Leu Lys Ser Asp Val Val Ser Gly Leu Thr Ile Ala Ser Leu Ala
 65                  70                  75                  80

Ile Pro Gln Gly Ile Ser Tyr Ala Asn Val Ala Asn Leu Pro Pro Ile
                 85                  90                  95

Val Gly Leu Tyr Ser Ser Phe Val Pro Pro Leu Val Tyr Ala Val Leu
            100                 105                 110

Gly Ser Ser Arg Asp Leu Ala Val Gly Pro Val Ser Ile Ala Ser Leu
        115                 120                 125

Ile Leu Gly Ser Met Leu Arg Gln Gln Val Ser Pro Val Asp Asp Pro
    130                 135                 140

Val Leu Phe Leu Gln Leu Ala Phe Ser Ser Thr Phe Phe Ala Gly Leu
145                 150                 155                 160

Phe Gln Ala Ser Leu Gly Ile Leu Arg Leu Gly Phe Ile Ile Asp Phe
                165                 170                 175

Leu Ser Lys Ala Thr Leu Ile Gly Phe Met Gly Gly Ala Ala Ile Ile
            180                 185                 190

Val Ser Leu Gln Gln Leu Lys Gly Leu Leu Gly Ile Thr His Phe Thr
        195                 200                 205

Lys His Met Ser Val Val Pro Val Leu Ser Ser Val Phe Gln His Thr
    210                 215                 220

Asn Glu Trp Ser Trp Gln Thr Ile Val Met Gly Val Cys Phe Leu Leu
225                 230                 235                 240

Phe Leu Leu Ser Thr Arg His Leu Ser Met Lys Lys Pro Lys Leu Phe
                245                 250                 255

Trp Val Ser Ala Gly Ala Pro Leu Leu Ser Val Ile Val Ser Thr Leu
            260                 265                 270

Leu Val Phe Val Phe Arg Ala Glu Arg His Gly Ile Ser Val Ile Gly
        275                 280                 285

Lys Leu Pro Glu Gly Leu Asn Pro Pro Ser Trp Asn Met Leu Gln Phe
    290                 295                 300

His Gly Ser His Leu Ala Leu Val Ala Lys Thr Gly Leu Val Thr Gly
305                 310                 315                 320

Ile Val Ser Leu Thr Glu Gly Ile Ala Val Gly Arg Thr Phe Ala Ala
                325                 330                 335

Leu Lys Asn Tyr His Val Asp Gly Asn Lys Glu Met Ile Ala Ile Gly
            340                 345                 350

Leu Met Asn Val Val Gly Ser Ala Thr Ser Cys Tyr Val Thr Thr Gly
        355                 360                 365

Ala Phe Ser Arg Ser Ala Val Asn Asn Asn Ala Gly Ala Lys Thr Ala
    370                 375                 380

Val Ser Asn Ile Val Met Ser Val Thr Val Met Val Thr Leu Leu Phe
385                 390                 395                 400

Leu Met Pro Leu Phe Glu Tyr Thr Pro Asn Val Val Leu Gly Ala Ile
                405                 410                 415
```

-continued

```
Ile Val Thr Ala Val Ile Gly Leu Ile Asp Leu Pro Ala Ala Cys His
            420                 425                 430

Ile Trp Lys Ile Asp Lys Phe Asp Phe Leu Val Met Leu Cys Ala Phe
        435                 440                 445

Phe Gly Val Ile Phe Leu Ser Val Gln Asn Gly Leu Ala Ile Ala Val
    450                 455                 460

Gly Leu Ser Leu Phe Lys Ile Leu Met Gln Val Thr Arg Pro Lys Met
465                 470                 475                 480

Val Ile Met Gly Asn Ile Pro Gly Thr Asp Ile Tyr Arg Asp Leu His
                485                 490                 495

His Tyr Lys Glu Ala Gln Arg Ile Pro Gly Phe Leu Val Leu Ser Ile
            500                 505                 510

Glu Ser Pro Val Asn Phe Ala Asn Ser Asn Tyr Leu Thr Glu Arg Thr
        515                 520                 525

Ser Arg Trp Ile Glu Glu Cys Glu Glu Glu Glu Ala Gln Glu Lys His
    530                 535                 540

Ser Ser Leu Gln Phe Leu Ile Leu Glu Met Ser Ala Val Ser Gly Val
545                 550                 555                 560

Asp Thr Asn Gly Val Ser Phe Phe Lys Glu Leu Lys Lys Thr Thr Ala
                565                 570                 575

Lys Lys Asp Ile Glu Leu Val Phe Val Asn Pro Leu Ser Glu Val Val
            580                 585                 590

Glu Lys Leu Gln Arg Ala Asp Glu Gln Lys Glu Phe Met Arg Pro Glu
        595                 600                 605

Phe Leu Phe Leu Thr Val Ala Glu Ala Val Ala Ser Leu Ser Leu Lys
    610                 615                 620

Gly Pro Ser Leu Ser Asn Val
625                 630


<210> SEQ ID NO 30
<211> LENGTH: 660
<212> TYPE: PRT
<213> ORGANISM: Hordeum vulgare

<400> SEQUENCE: 30

Met Pro Arg Thr Val Ser Asp Gly Gly Glu Asp Phe Asp Gly Asp Val
  1               5                  10                  15

Cys Ser Gln Thr Ala Ser Gln Arg His Thr Asp Ser Thr His His His
            20                  25                  30

His Gly Tyr Lys Val Gly Phe Pro Pro Ala Lys Gly Val Phe Ala Glu
        35                  40                  45

Phe Ala Glu Gly Val Lys Glu Thr Phe Phe Ala Asp Asp Pro Leu Arg
    50                  55                  60

Glu Tyr Lys Asp Gln Pro Arg Ser Lys Lys Leu Trp Leu Ser Leu Val
 65                  70                  75                  80

His Leu Phe Pro Val Leu Asp Trp Ser Arg Ser Tyr Thr Phe Gly Lys
                85                  90                  95

Phe Lys Gly Asp Leu Val Ala Gly Leu Thr Ile Ala Ser Leu Cys Ile
            100                 105                 110

Pro Gln Asp Ile Gly Tyr Ala Lys Leu Ala Asn Leu Gln Pro His Val
        115                 120                 125

Gly Leu Tyr Ser Ser Phe Val Pro Pro Leu Ile Tyr Ala Leu Met Gly
    130                 135                 140

Ser Ser Arg Asp Ile Ala Ile Gly Pro Val Ala Val Val Ser Leu Leu
```

-continued

```
145                 150                 155                 160

Leu Gly Thr Leu Leu Gln Glu Glu Ile Asp Pro Val Lys Asn Pro Leu
                165                 170                 175

Glu Tyr Ser Arg Leu Ala Phe Thr Ala Thr Phe Phe Ala Gly Ile Thr
            180                 185                 190

Gln Ala Met Leu Gly Phe Phe Arg Leu Gly Phe Ile Ile Glu Phe Leu
        195                 200                 205

Ser His Ala Ala Ile Val Gly Phe Met Ala Gly Ala Ala Ile Thr Ile
    210                 215                 220

Ala Leu Gln Gln Leu Lys Gly Leu Leu Gly Ile Ala Lys Phe Thr Lys
225                 230                 235                 240

Lys Ser Asp Ile Ile Ser Val Met Glu Ser Val Trp Gly Asn Val Gln
                245                 250                 255

His Gly Trp Asn Trp Gln Thr Ile Leu Ile Gly Ser Ser Phe Leu Ala
            260                 265                 270

Phe Leu Leu Thr Thr Lys Tyr Ile Ala Lys Lys Asn Lys Lys Leu Phe
        275                 280                 285

Trp Val Ser Ala Ile Ala Pro Leu Ile Ser Val Val Ile Ser Thr Phe
    290                 295                 300

Cys Val Tyr Ile Thr Arg Ala Asp Lys Gln Gly Val Ala Ile Val Lys
305                 310                 315                 320

Asn Ile Lys Gln Gly Ile Asn Pro Pro Ser Phe Asp Leu Ile Tyr Trp
                325                 330                 335

Ser Gly Pro Tyr Leu Ala Lys Gly Phe Arg Ile Gly Val Val Ser Gly
            340                 345                 350

Met Val Ala Leu Thr Glu Ala Ile Ala Ile Gly Arg Thr Phe Ala Ala
        355                 360                 365

Met Lys Asp Tyr Gln Ile Asp Gly Asn Lys Glu Met Val Ala Leu Gly
    370                 375                 380

Thr Met Asn Ile Val Gly Ser Met Thr Ser Cys Tyr Val Ala Thr Gly
385                 390                 395                 400

Ser Phe Ser Arg Ser Ala Val Asn Tyr Met Ala Gly Cys Lys Thr Ala
                405                 410                 415

Val Ser Asn Val Val Met Ala Ile Val Val Met Leu Thr Leu Leu Leu
            420                 425                 430

Ile Thr Pro Leu Phe Lys Tyr Thr Pro Asn Ala Ile Leu Ala Ser Ile
        435                 440                 445

Ile Ile Asn Ala Val Val Asn Leu Val Asp Tyr Glu Thr Ala Tyr Leu
    450                 455                 460

Ile Trp Lys Val Asp Lys Met Asp Phe Val Ala Leu Leu Gly Ala Phe
465                 470                 475                 480

Phe Gly Val Val Phe Ala Ser Val Glu Tyr Gly Leu Leu Ile Ala Val
                485                 490                 495

Ala Ile Ser Leu Gly Lys Ile Leu Leu Gln Val Thr Arg Pro Arg Thr
            500                 505                 510

Ala Leu Leu Gly Asn Leu Pro Arg Thr Thr Ile Tyr Arg Asn Val Glu
        515                 520                 525

Gln Tyr Pro Glu Ala Thr Lys Val Pro Gly Val Met Ile Val Arg Val
    530                 535                 540

Asp Ser Ala Ile Tyr Phe Thr Asn Ser Asn Tyr Val Lys Glu Arg Ile
545                 550                 555                 560

Leu Arg Trp Leu Arg Asp Glu Glu Glu Gln Gln Gln Glu Gln Lys Leu
                565                 570                 575
```

-continued

Ser Lys Thr Glu Phe Leu Ile Val Glu Leu Ser Pro Val Thr Asp Ile
580 585 590

Asp Thr Ser Gly Ile His Ala Leu Glu Glu Leu Leu Lys Ala Leu Glu
595 600 605

Lys Arg Lys Ile Gln Leu Ile Leu Ala Asn Pro Gly Pro Ala Val Ile
610 615 620

Gln Lys Leu Arg Ser Ala Lys Phe Thr Asp Leu Ile Gly Asp Asp Lys
625 630 635 640

Ile Phe Leu Ser Val Gly Asp Ala Val Lys Lys Phe Ala Pro Lys Ser
645 650 655

Ser Leu Asn Val
660

<210> SEQ ID NO 31
<211> LENGTH: 685
<212> TYPE: PRT
<213> ORGANISM: Arabidopsis thaliana

<400> SEQUENCE: 31

Met Ser Tyr Ala Ser Leu Ser Val Lys Asp Leu Thr Ser Leu Val Ser
1 5 10 15

Arg Ser Gly Thr Gly Ser Ser Ser Ser Leu Lys Pro Pro Gly Gln Thr
20 25 30

Arg Pro Val Lys Val Ile Pro Leu Gln His Pro Asp Thr Ser Asn Glu
35 40 45

Ala Arg Pro Pro Ser Ile Pro Phe Asp Asp Ile Phe Ser Gly Trp Thr
50 55 60

Ala Lys Ile Lys Arg Met Arg Leu Val Asp Trp Ile Asp Thr Leu Phe
65 70 75 80

Pro Cys Phe Arg Trp Ile Arg Thr Tyr Arg Trp Ser Glu Tyr Phe Lys
85 90 95

Leu Asp Leu Met Ala Gly Ile Thr Val Gly Ile Met Leu Val Pro Gln
100 105 110

Ala Met Ser Tyr Ala Lys Leu Ala Gly Leu Pro Pro Ile Tyr Gly Leu
115 120 125

Tyr Ser Ser Phe Val Pro Val Phe Val Tyr Ala Ile Phe Gly Ser Ser
130 135 140

Arg Gln Leu Ala Ile Gly Pro Val Ala Leu Val Ser Leu Leu Val Ser
145 150 155 160

Asn Ala Leu Gly Gly Ile Ala Asp Thr Asn Glu Glu Leu His Ile Glu
165 170 175

Leu Ala Ile Leu Leu Ala Leu Leu Val Gly Ile Leu Glu Cys Ile Met
180 185 190

Gly Leu Leu Arg Leu Gly Trp Leu Ile Arg Phe Ile Ser His Ser Val
195 200 205

Ile Ser Gly Phe Thr Ser Ala Ser Ala Ile Val Ile Gly Leu Ser Gln
210 215 220

Ile Lys Tyr Phe Leu Gly Tyr Ser Ile Ala Arg Ser Ser Lys Ile Val
225 230 235 240

Pro Ile Val Glu Ser Ile Ile Ala Gly Ala Asp Lys Phe Gln Trp Pro
245 250 255

Pro Phe Val Met Gly Ser Leu Ile Leu Val Ile Leu Gln Val Met Lys
260 265 270

His Val Gly Lys Ala Lys Lys Glu Leu Gln Phe Leu Arg Ala Ala Ala

-continued

```
        275                 280                 285

Pro Leu Thr Gly Ile Val Leu Gly Thr Thr Ile Ala Lys Val Phe His
    290                 295                 300

Pro Pro Ser Ile Ser Leu Val Gly Glu Ile Pro Gln Gly Leu Pro Thr
305                 310                 315                 320

Phe Ser Phe Pro Arg Ser Phe Asp His Ala Lys Thr Leu Leu Pro Thr
                325                 330                 335

Ser Ala Leu Ile Thr Gly Val Pro Ile Leu Glu Ser Val Gly Ile Ala
            340                 345                 350

Lys Ala Leu Ala Ala Lys Asn Arg Tyr Glu Leu Asp Ser Asn Ser Asp
        355                 360                 365

Leu Phe Gly Leu Gly Val Ala Asn Ile Leu Gly Ser Leu Phe Ser Ala
    370                 375                 380

Tyr Pro Ala Thr Gly Ser Phe Ser Arg Ser Ala Val Asn Asn Glu Ser
385                 390                 395                 400

Glu Ala Lys Thr Gly Leu Ser Gly Leu Ile Thr Gly Ile Ile Ile Gly
                405                 410                 415

Cys Ser Leu Leu Phe Leu Thr Pro Met Phe Lys Tyr Ile Pro Gln Cys
            420                 425                 430

Ala Leu Ala Ala Ile Val Ile Ser Ala Val Ser Gly Leu Val Asp Tyr
        435                 440                 445

Asp Glu Ala Ile Phe Leu Trp Arg Val Asp Lys Arg Asp Phe Ser Leu
    450                 455                 460

Trp Thr Ile Thr Ser Thr Ile Thr Leu Phe Phe Gly Ile Glu Ile Gly
465                 470                 475                 480

Val Leu Val Gly Val Gly Phe Ser Leu Ala Phe Val Ile His Glu Ser
                485                 490                 495

Ala Asn Pro His Ile Ala Val Leu Gly Arg Leu Pro Gly Thr Thr Val
            500                 505                 510

Tyr Arg Asn Ile Lys Gln Tyr Pro Glu Ala Tyr Thr Tyr Asn Gly Ile
        515                 520                 525

Val Ile Val Arg Ile Asp Ser Pro Ile Tyr Phe Ala Asn Ile Ser Tyr
    530                 535                 540

Ile Lys Asp Arg Leu Arg Glu Tyr Glu Val Ala Val Asp Lys Tyr Thr
545                 550                 555                 560

Asn Arg Gly Leu Glu Val Asp Arg Ile Asn Phe Val Ile Leu Glu Met
                565                 570                 575

Ser Pro Val Thr His Ile Asp Ser Ser Ala Val Glu Ala Leu Lys Glu
            580                 585                 590

Leu Tyr Gln Glu Tyr Lys Thr Arg Asp Ile Gln Leu Ala Ile Ser Asn
        595                 600                 605

Pro Asn Lys Asp Val His Leu Thr Ile Ala Arg Ser Gly Met Val Glu
    610                 615                 620

Leu Val Gly Lys Glu Trp Phe Phe Val Arg Val His Asp Ala Val Gln
625                 630                 635                 640

Val Cys Leu Gln Tyr Val Gln Ser Ser Asn Leu Glu Asp Lys His Leu
                645                 650                 655

Ser Phe Thr Arg Arg Tyr Gly Gly Ser Asn Asn Asn Ser Ser Ser Ser
            660                 665                 670

Asn Ala Leu Leu Lys Glu Pro Leu Leu Ser Val Glu Lys
        675                 680                 685
```

GENES ENCODING SULFATE ASSIMILATION PROTEINS

This application claims the benefit of U.S. Provisional Application No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) *PANS* 92(20):9373–9377). Once sulfur is in the cell sulfate adenylyltransferase (ATP sulfurylase) (Bolchia et al. (1999) *Plant Mol Biol.* 39(3):527–537) catalyzes the first step in assimilation, converting the inorganic sulfur into an organic form, adenosine-5' phospho-sulfate (APS). Next, several enzymes further modify organic sulfur for use in the biosynthesis of cysteine and methionine. For example, adenylylsulfate kinase (APS kinase), catalyzes the conversion of APS to the biosynthetic intermediate PAPS (3'-phospho-adenosine-5' phosphosulfate) (Arz et al. (1994) *Biochim. Biophy.* Acta 1218(3):447–452). APS reductase (5' adenylyl phosphosulphate reductase) is utilized in an alternative pathway, resulting in an inorganic but cellularly bound (bound to a carrier), form of sulfur (sulfite) (Setya et al. (1996) *PANS* 93(23):13383–13388). Sulfite reductase further reduces the sulfite, still attached to the carrier, to sulfide and serine 0-acetyltransferase converts serine to O-acetylserine, which will serve as the backbone to which the sulfide will be transferred to from the carrier to form cysteine (Yonelcura-Sakakibara et al. (1998) *J. Biolchem.* 124(3):615–621 and Saito et al. (1995) *J. Biol. Chem.* 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

SUMMARY OF THE INVENTION

The instant invention relates to isolated nucleic acid fragments encoding sulfate assimilation proteins.

Specifically, this invention concerns an isolated nucleic acid fragment encoding a sulfate permease and an isolated nucleic acid fragment that is substantially similar to an isolated nucleic acid fragment encoding a sulfate permease. In addition, this invention relates to a nucleic acid fragment that is complementary to the nucleic acid fragment encoding sulfate permease. An additional embodiment of the instant invention pertains to a polypeptide encoding all or a substantial portion of a sulfate permease.

In another embodiment, the instant invention relates to a chimeric gene encoding a, or to a chimeric gene that comprises a nucleic acid fragment that is complementary to a nucleic acid fragment encoding a sulfate permease, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a sulfate permease, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a sulfate permease in a transformed host cell comprising: transforming a host cell with a chimeric gene comprising a nucleic acid fragment encoding a sulfate permease; and b) growing the transformed host cell under conditions that are suitable for expression of the chimeric gene wherein expression of the chimeric gene results in production of altered levels of sulfate permease in the transformed host cell.

An addition embodiment of the instant invention concerns a method for obtaining a nucleic acid fragment encoding all or a substantial portion of an amino acid sequence encoding a sulfate permease.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A, 1B, 1C, 1D, 1E, 1F, 1G, 1H, 1I, 1J, 1K, 1L, and 1M show a comparison of the amino acid sequences set forth in SEQ ID NOs:2, 4, 6, 8, 10, 12, 14, 16, 18, 20 and 22 and the *Arabidopsis thaliana* (SEQ ID NOs:24 (gi 2285885), 26 (gi 2967456), 28 (gi 2130944), 29 (gi 4579913) and 31 (gi 2626753)), *Hordeum vulgare* (SEQ ID NO:30), *Stylosanthes hamata* (SEQ ID NO:25), *Sporobolus stapflanus* (SEQ ID NO:23) and *Zea mays* (SEQ ID NO:27) sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| Sulfate Assimilation Proteins | | | |
|---|---|---|---|
| | | SEQ ID NO: | |
| Protein | Clone Designation | (Nucleotide) | (Amino Acid) |
| Sulfate Permease | Contig composed of:<br>cbn10.pk0062.b10<br>cco1n.pk081.h21<br>cco1n.pk092.12<br>csc1c.pk005.j3<br>p0004.cblej58r<br>p0089.csdch19r<br>p0094.csssg12r<br>p0121.cfrmx30r<br>p0128.cpicz09r | 1 | 2 |
| Sulfate Permease | Contig composed of:<br>cr1n.pk0015.a2<br>p0006.cbyvs25rb<br>p0072.comhc25r<br>p0091.cmard29r<br>p0092.chwat43r | 3 | 4 |
| Sulfate Permease | cs1.pk0063.f8 | 5 | 6 |
| Sulfate Permease | hel1.pk0011.f1 | 7 | 8 |
| Sulfate Permease | rl0n.pk0076.c10 | 9 | 10 |
| Sulfate Permease | rlr2.pk0022.d9 | 11 | 12 |
| Sulfate Permease | rls48.pk0003.a9 | 13 | 14 |
| Sulfate Permease | ses2w.pk0031.b3 | 15 | 16 |
| Sulfate Permease | sfl1.pk0043.g10 | 17 | 18 |
| Sulfate Perrnease | wlk1.pk0028.e1 | 19 | 20 |
| Sulfate Permease | wlm4.pk0016.a11 | 21 | 22 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemically Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell. "Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available. "Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the MRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastic types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sulfate assimilation proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sulfate permease enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of enzyme in question as a possible limiting step, thus increasing the potential flux through the pathway to the essential amino acids. This will allow the engineering of plant tissues with increases levels of these amino acids, which now often must be added a supplements to animal feed in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rely. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or co-suppression (U.S. Pat. Nos. 5,190,931, 5,107,065 and 5,283,323). An antisense or co-suppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1). 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Seguencing of cDNA Clones cDNA libraries representing mRNAs from various artichoke, corn, rice, soybean and wheat tissues were prepared. The characteristics of the libraries are described below.

TABLE 2 cDNA Libraries from Artichoke, Corn, Rice, Soybean and Wheat

| Library | Tissue | Clone |
|---|---|---|
| cbn10 | Corn (*Zea mays* L.) developing kernel (embryo and endosperm); 10 days after pollination | cbn10.pk0062.b10 |
| cco1n | Corn (*Zea mays* L.) cob of 67 day old plants grown in green house* | cco1n.pk081.h21<br>cco1n.pk092.12 |
| cr1n | Corn (*Zea mays* L.) root from 7 day seedlings grown in light* | cr1n.pk0015.a2 |
| csc1c | Corn (*Zea mays* L., B73) 20 day seedling (germination under cold stress) | csc1c.pk005.j3 |
| cs1 | Corn (*Zea mays* L.) leaf, sheath 5 week old plant | cs1.pk0063.f8 |
| hel1 | Jerusalem artichoke (*Helianthus tuberosus*) tuber at filling stage | hel1.pk0011.f1 |
| p0004 | Corn (*Zea mays* L.) immature ear | p0004.cblej58r |
| p0089 | Corn (*Zea mays* L.) 10 day Seedling (germination under cold stress)* | p0089.csdch19r |
| p0094 | Corn (*Zea mays* L.) leaf collars for the ear leaf and the next leaf above and below* | p0094.csssg12r |
| p0121 | Corn (*Zea mays* L.) shank tissue collected from ears 5 days after pollination* | p0121.cfrmx30r |
| p0128 | Corn (*Zea mays* L.) primary and secondary immature ear | p0128.cpicz09r |
| p0006 | Corn (*Zea mays* L.) young shoot | p0006.cbyvs25rb |
| p0072 | Corn (*Zea mays* L.) 14 days after planting etiolated seedling: mesocotyl | p0072.comhc25r |
| p0091 | Corn (*Zea mays* L.) germinating maize seeds: 2 & 3 day roots, under normal growth condition* | p0091.cmard29r |
| p0092 | Corn (*Zea mays* L.) husks, growth conditions: field; untreated tissues* | p0092.chwat43r |
| r10n | Rice (*Oryza sativa* L.) 15 day leaf | r10n.pk0076.c10 |
| rlr2 | Rice (*Oryza sativa* L.) leaf (15 days after germination) 2 hrs after infection of strain *Magaporthe grisea* 4360-R-67 (avr2-yamo); Susceptible | rlr2.pk0022.d9 |
| rls48 | Rice (*Oryza sativa* L.) leaf (15 days after germinations) 48 hours after infection of strain Magaporthe grisea 4360-R-67 (avr2-yamo); Susceptible | rls48.pk0003.a9 |
| ses2w | Soybean (*Glycine max* L.) embryogenic suspension 2 weeks after subculture | ses2w.pk0031.b3 |
| sfl1 | Soybean (*Glycine max* L.) immature flower | sfl1.pk0043.g10 |
| wlk1 | wheat (*Triticum aestivum* L.) seedlings 1 hr after treatment with fungicide** | wlk1 .pk0028.e1 |
| wlm4 | Wheat (*Triticum aestivum* L.) seedlings 4 hr after inoculation w/*E. graminis* | wlm4.pk0016.a11 |

*These libraries were normalized essentially as described in U.S. Pat. No. 5,482,845, incorporated herein by reference.
**Fungicide: Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP*XR vectors according to the manufacturer's protocol (Stratagene Cloning Systems, La Jolla, Calif.) The Uni-ZAP*XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of CDNA Clones Encoding Sulfate Permease

The BLASTX search using the EST sequences from clones listed in Table 3 revealed similarity of the polypeptides encoded by the cDNAs to sulfate permease from *Arabidopsis thaliana* (NCBI Identifier No. gi 2967456, gi 2285885, gi 2130944, gi 4579913, gi 2626753), *Sporobolus stapflanus* (NCBI Identifier No. gi 1907270), *Zea mays* (NCBI Identifer No. gi 2738752), *Hordeum vulgare* (NCBI Identifier No. gi 1217967) and *Stylosanthes hamata* (NCBI Identifier No. gi 1711618). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Arabidopsis thaliana, Sporobolus stapfianus, Zea mays, Hordeum vulgare* and *Stylosanthes hamata* Sulfate Permease

| Clone | Status | BLAST pLog Score |
|---|---|---|
| Contig composed of:<br>cbn10.pk0062.b10<br>cco1n.pk081.h21<br>cco1n.pk092.12<br>csc1c.pk005.j3<br>p0004.cblej58r<br>p0089.csdch19r<br>p0094.csssg12r<br>p0121.cfrmx30r<br>p0128.cpicz09r | Contig | >254.00 (gi 1907270) |
| Contig composed of:<br>cr1n.pk0015.a2<br>p0006.cbyvs25rb<br>p0072.comhc25r<br>p0091.cmard29r<br>p0092.chwat43r | Contig | >254.00 (gi 2285885) |
| cs1.pk0063.f8 | FIS | 108.00 (gi 1711618) |
| hel1.pk0011.f1 | FIS | 77.70 (gi 2967456) |
| rl0n.pk0076.c10 | EST | 65.20 (gi 2738752) |
| rlr2.pk0022.d9 | EST | 13.40 (gi 2130944) |
| rls48.pk0003.a9 | EST | 61.00 (gi 1711618) |
| ses2w.pk0031.b3 | FIS | >254.00 (gi 4579913) |
| sfl1.pk0043.g10 | FIS | >254.00 (gi 2285885) |
| wlk1.pk0028.e1 | EST | >254.00 (gi 1217967) |
| wlm4.pk0016.a11 | EST | >250.00 (gi 2626753) |

FIG. 1 presents an alignment of the amino acid sequences set forth in SEQ ID NOs:2, 4, 6, 8, 10, 12, 14, 16, 18, 20 and 22 and the *Arabidopsis thaliana* (SEQ ID NOs:24 (gi 2285885), 26 (gi 2967456), 28 (gi 2130944), 29 (gi 4579913) and 31 (gi 2626753)), *Hordeum vulgare* (SEQ ID NO:30), *Stylosanthes hamata* (SEQ ID NO:25), *Sporobolus stapfianus* (SEQ ID NO:23) and *Zea mays* (SEQ ID NO:27) sequences.

The data in Table 4 represents a calculation of the percent identity of the amino acid sequences set forth in SEQ ID NOs:2, 4, 6, 8, 10, 12, 14, 16, 18, 20 and 22 and the *Arabidopsis thaliana* (SEQ ID NOs:24 (gi 2285885), 26 (gi 2967456), 28 (gi 2130944), 29 (gi 4579913) and 31 (gi 2626753)), *Hordeum vulgare* (SEQ ID NO:30), *Stylosanthes hamata* (SEQ ID NO:25), *Sporobolus stapfianus* (SEQ ID NO:23) and *Zea mays* (SEQ ID NO:27) sequences.

TABLE 4

Percent Identity of Amino Acid Sequences Deduced From the Nucleotide Sequences of cDNA Clones Encoding Polypeptides Homologous to *Arabidopsis thaliana, Sporobolus stapfianus, Zea mays, Hordeum vulgare* and *Stylosanthes hamata* Sulfate Permease Sequences

| SEQ ID NO. | Percent Identity to |
|---|---|
| 2 | 80.2% (gi 1907270) |
| 4 | 70.0% (gi 2285885) |
| 6 | 59.0% (gi 1711618) |
| 8 | 59.0% (gi 2967456) |
| 10 | 69.0% (gi 2738752) |
| 12 | 33.0% (gi 2130944) |
| 14 | 67.0% (gi 1711618) |
| 16 | 61.0% (gi 4579913) |
| 18 | 75.0% (gi 2285885) |
| 20 | 71.0% (gi 1217967) |
| 22 | 73.0% (gi 2626753) |

Sequence alignments and percent identity calculations were performed using the Magalign program of the LASARGENE bioinformatics computing suite (DNASTAR Inc., Madison Wis.) Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a sustantial portion of a sulfate permease. These sequences represent the first artichoke, corn, rice, soybean wheat sequences encoding sulfate permease.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Ncol or Smal) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb Ncol-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-Ncol promoter fragment of the maize 27 kD zein gene and a 0.96 kb SmaI-Sall fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of $\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(983) Gene 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. Coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTGTM low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into D115 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL2 1 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:

(a) a nucleotide sequence encoding a polypeptide having sulfate permease activity, wherein the amino acid sequence of the polypeptide and the amino acid sequence of SEQ ID NO:2 have at least 85% sequence identity based on the Clustal alignment method with multiple alignment default parameters of GAP PENALTY=10 and GAP LENGTH PENALTY=10 and pairwise alignment default parameters of KTUPLE=1, GAP PENALTY=3, WISNDOW=5 and DIAGONALS SAVED=5, or (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:2 have at least 90% sequence identity based on the Clustal alignment method with the multiple alignment default parameters and the pairwise alignment default parameters.

3. The polynucleotide of claim 1, wherein the amino acid sequence of the polypeptide and the amino acid sequence of SEQ ID NO:2 have at least 95% sequence identity based on the Clustal alignment method with the multiple alignment default parameters and the pairwise alignment default parameters.

4. The polynucleotide of claim 1, wherein the polypeptide comprises the amino acid sequence of SEQ ID NO:2.

5. The polynucleotide of claim 1, wherein the nucleotide sequence comprises the nucleotide sequence of SEQ ID NO:1.

6. A vector comprising the polynucleotide of claim 1.

7. A recombinant DNA construct comprising the polynucleotide of claim 1 operably linked to at least one regulatory sequence.

8. A method for transforming a cell comprising transforming a cell with the polynucleotide of claim 1.

9. A cell comprising the recombinant DNA construct of claim 7.

10. A method for producing a plant comprising transforming a plant cell with the polynucleotide of claim 1 and regenerating a plant from the transformed plant cell.

11. A plant comprising the recombinant DNA construct of claim 1.

12. A seed comprising the recombinant DNA construct of claim 1.

* * * * *

UNITED STATES PATENT AND TRADEMARK OFFICE

CERTIFICATE OF CORRECTION

PATENT NO. : 6,696,292 B1 Page 1 of 1
DATED : February 24, 2004
INVENTOR(S) : Allen Stephen M. and Falco Saverio Carl It is certified that error appears in the above-identified patent and that said Letters Patent is hereby corrected as shown below:

Title page,
Item [75], Inventors, delete "Catherine J. Thorpe, Cambridge (GB)"
Item [56], References Cited, OTHER PUBLICATIONS, add -- Andreas Bruhl et al., Biochimica et Biophysica Acta, Vol. 1295:119-124, 1996, A cDNA clone from Arabidopsis thaliana encoding plasticidic ferredoxin: sulfite reductase --.

Signed and Sealed this

Twenty-eighth Day of September, 2004

JON W. DUDAS
*Director of the United States Patent and Trademark Office*